United States Patent [19]
Pitroda

[11] Patent Number: 5,884,271
[45] Date of Patent: *Mar. 16, 1999

[54] DEVICE, SYSTEM AND METHODS OF CONDUCTING PAPERLESS TRANSACTIONS

[76] Inventor: Satyan G. Pitroda, 1480 Golden Bell Ct., Downers Grove, Ill. 60515

[ * ] Notice: The term of this patent shall not extend beyond the expiration date of Pat. No. 5,590,038.

[21] Appl. No.: 708,555

[22] Filed: Sep. 6, 1996

Related U.S. Application Data

[63] Continuation-in-part of Ser. No. 262,307, Jun. 20, 1994.

[51] Int. Cl.$^6$ .................................................. G06F 17/60
[52] U.S. Cl. ............................................... 705/1; 395/24
[58] Field of Search ................................. 395/241; 705/1

[56] References Cited

U.S. PATENT DOCUMENTS

| | | | |
|---|---|---|---|
| Re. 28,081 | 7/1974 | Travioli | 235/61.11 E |
| 4,305,059 | 12/1981 | Benton | 340/825.33 |
| 4,341,951 | 7/1982 | Benton | 235/379 |
| 4,454,414 | 6/1984 | Benton | 235/379 |
| 4,491,725 | 1/1985 | Prichard | 364/408 |
| 4,523,087 | 6/1985 | Benton | 235/379 |
| 4,575,621 | 3/1986 | Dreifus | 235/380 |
| 4,634,845 | 1/1987 | Hale et al. | 235/350 |
| 4,650,981 | 3/1987 | Foletta | 235/449 |
| 4,689,478 | 8/1987 | Hale et al. | 235/380 |
| 4,692,601 | 9/1987 | Nakano | 235/380 |
| 4,705,211 | 11/1987 | Honda et al. | 235/380 |
| 4,739,295 | 4/1988 | Hayashi et al. | 235/492 |
| 4,833,595 | 5/1989 | Iijima | 364/200 |
| 4,837,422 | 6/1989 | Detloff et al. | 235/380 |
| 4,849,613 | 7/1989 | Eisele | 235/379 |
| 4,849,614 | 7/1989 | Watanabe et al. | 235/380 |
| 4,858,121 | 8/1989 | Barber et al. | 364/406 |
| 4,891,506 | 1/1990 | Yoshimatsu | 235/492 |
| 4,910,774 | 3/1990 | Barakat | 380/30 |
| 4,910,775 | 3/1990 | Yves et al. | 380/25 |

(List continued on next page.)

FOREIGN PATENT DOCUMENTS 2255934   11/1992   United Kingdom .

OTHER PUBLICATIONS

Sprint Priority Gold$^{sm}$ Newsletter, Mar. 11, 1994,—"the Voice Fōncard$^{smn}$" 1994 Sprint Communications Co. L.P. (2 pgs).

PC Magazine—Mar. 29, 1994, Trends, Trends & Technology Shaping the Personal Computer Market, "The PC in Your Wallet", publication (1 page).

Business Life Magazine, Dec./Jan. 1994/95, "The Era of the Smart Card", publication (4 pages).

Mondex Magazine—The World of Mondex Global Electronic Cash, Summer 1996, "What's up doc?—The Smart Way to pay for Infotainment", publication (3 pages).

*Primary Examiner*—Allen R. MacDonald
*Assistant Examiner*—M. Irshadullah

[57] ABSTRACT

A universal electronic transaction card ("UET card") is capable of serving as a number of different credit cards, bank cards, identification cards, employee cards, medical and health care management cards and the like. The UET card includes storage elements, an input interface, a processor, a display, and a communications interface. In a preferred embodiment, the UET card stores transactional information to eliminate paper receipts and includes security features to prevent unauthorized use. The UET card may also be used to replace conventional currency and traveler's checks, and may be configured to store and display promotional information, such as advertising and incentives.

The invention also includes systems for using UET cards, for example, health care management systems, communication interface units, and methods for using the same, including methods of issuing an account authorization to a UET card, a method of transferring transactional and account information between a UET card and a personal computer or a mainframe computer, a method of using the UET card as a remote terminal for a mainframe computer, and a method of conducting an electronic transaction.

32 Claims, 18 Drawing Sheets

U.S. PATENT DOCUMENTS

| | | | |
|---|---|---|---|
| 4,918,631 | 4/1990 | Hara et al. | 364/708 |
| 4,928,001 | 5/1990 | Masada | 235/492 |
| 4,973,828 | 11/1990 | Naruse et al. | 235/380 |
| 4,983,816 | 1/1991 | Iijima | 235/379 |
| 5,015,830 | 5/1991 | Masuzawa et al. | 235/441 |
| 5,017,766 | 5/1991 | Tamada et al. | 235/492 |
| 5,023,908 | 6/1991 | Weiss | 380/23 |
| 5,055,662 | 10/1991 | Hasegawa | 235/492 |
| 5,055,968 | 10/1991 | Nishi et al. | 361/395 |
| 5,068,521 | 11/1991 | Yamaguchi | 235/492 |
| 5,150,420 | 9/1992 | Haraguchi | 235/380 |
| 5,153,842 | 10/1992 | Dlugos, Sr. et al. | 235/380 |
| 5,157,247 | 10/1992 | Takahira | 235/492 |
| 5,168,151 | 12/1992 | Nara | 235/492 |
| 5,189,287 | 2/1993 | Parienti | 235/375 |
| 5,218,188 | 6/1993 | Hanson | 235/375 |
| 5,276,311 | 1/1994 | Hennige | 235/492 |
| 5,301,105 | 4/1994 | Cummings, Jr. | 364/401 |
| 5,590,038 | 12/1996 | Pitroda | 395/241 |

| ☐ TYPE | ☐ PRINT | ☐ ERASE |
|---|---|---|
| ☐ HELP | ☐ SEC | ☐ ← |
| ☐ ↑ | ☐ ↓ | ☐ → |
| ☐ SUMMARY | ☐ ACCT/PAY | ☐ WEEKLY |
| ☐ MONTHLY | ☐ YEARLY | ☐ LAST USED |
| ☐ CREDIT LIMIT | ☐ BALANCE | ☐ LOAD PC |
| ☐ WRITE CHECKS | ☐ WITHDRAW | ☐ DEPOSITS |
| ☐ PERIODIC CHECKS | ☐ STATEMENT | ☐ ATM |
| ☐ WRITE/TYPE | ☐ SEARCH | ☐ REMIND |
| | ☐ SPECIAL COMMANDS | |

FIG. 18

|   |   |   |   |   |   |   |
|---|---|---|---|---|---|---|
| A | B | C | D |   |   |   |
|   |   |   |   |   |   | Z |
| 0 | 1 | 2 |   |   | 8 | 9 | * |

FIG. 26

MISC.
- ☐ to do        ☐ to tel.
- ☐ to see/mtg.  ☐ friends
- ☐ clock        ☐ calendar
- ☐ projects     ☐ errand
- ☐ finance      ☐ events

KEYS

FIG. 28

DEVICE, SYSTEM AND METHODS OF CONDUCTING PAPERLESS TRANSACTIONS

This application is a continuation in part of application Ser. No. 08/262,307, filed Jun. 20, 1994.

BACKGROUND OF THE INVENTION

This invention relates to a universal electronic transaction card ("UET card") for storing, transmitting and receiving personal, accounting and transactional information, to a UET card and communications systems, and to an electronic transaction system which utilizes UET cards. This invention also relates to a health care system utilizing UET cards. This invention also relates to methods of issuing an account authorization to a UET card, a method of transferring transactional and account information between a UET card and a personal computer or a mainframe computer, a method of using the UET card as a remote terminal for a mainframe computer, and a method of conducting an electronic transaction. The UET card of the present invention is capable of functioning as a number of different credit cards or other transaction or identification cards, which provides the user of the UET card with the capability of selecting one of many such cards for use in a particular transaction. The UET card of this invention has universal application for all personal and financial transactions, such as normal credit card usage of the type commonly associated with MASTERCARD, VISA, AMERICAN EXPRESS or automatic banking transactions (known as "ATM" transactions); health service transactions, such as physicians' services, hospital services, or home health care services; personal identification, including social security number, signature, photograph, and other personal information; employee information, such as employee identification numbers; and license information, including drivers licenses, vehicle registrations, professional licenses, and the like.

Presently, plastic cards are used for a variety of transactions, such as credit card purchases, and automatic banking transactions. Such credit cards include a magnetic strip that contains coded information for account information and, in some cases, a security code. The coded information on the magnetic strips is read by a device in the possession of a merchant, which transmits the account information to a central computer, which determines whether the account number is valid and whether the purchase is within the amount of credit available for that account. If the transaction is authorized, the card user receives a paper receipt as his or her record of the transaction, and the retail merchant also keeps a copy of the receipt as a record of the transaction. Later, usually within 30 days, the card user receives a written statement, which, in the case of a credit card, contains an invoice for payment. The user must then write a check to the credit card company to pay the amount due on the account. The disadvantage of the foregoing system is that at least two written documents are generated for the credit card user, at a substantial cost to the credit card institution.

In the case of ATM banking machines, a banking card is inserted into the card reader of the machine, which reads the coded account information and security code. The card user then enters a security code. If the security code is correct, the card user is then able to perform a banking transaction in which he or she may either deposit money, withdraw money, or check account balances. The ATM card user receives a paper receipt for the transaction. Later, the ATM card user also receives a paper record of all of his or her transactions for the month from the banking institution.

Every day, at least tens of millions of credit card and ATM transactions take place. Each transaction gives rise to the creation of several pieces of paper relating to billing for the goods or services purchased by credit card. Elimination of all or a substantial amount of paper associated with those transactions would reduce the costs of providing credit card services and would reduce the amount of waste generated and energy used as a result, and would improve the environment. Further, conversion of the manual billing system could eliminate substantial labor costs and also reduce the amount of human error in credit card transactions.

The same is true of the health care industry. A substantial amount of paper is generated by the health care industry, including insurance cards, medical identification cards, medical bills, medical history reports, and the like. A substantial amount of personal health care information must be manually entered for each visit by a patient to a health care provider. Each visit usually results in filling out one or more insurance forms that are, in turn, sent to insurance companies for processing. Approximately 15% of the cost of health care is spent on insurance companies who process payments and claims. The substantial reduction or elimination of paper work associated with health care, and the conversion to a paperless billing system could greatly reduce the labor costs associated with health care, and thereby reduce health care expenses considerably.

Most people carry a substantial number of cards, including multiple credit cards, insurance cards, drivers' licenses, airline cards, check identification cards, ATM cards, and employee identification cards. Carrying a substantial number of such cards is inconvenient. Financial accounting associated with these cards related to paying bills, keeping track of accounts, budgeting, planning and the like, is manual, cumbersome, time consuming, and difficult to manage and maintain. Further, such cards are replaced on a periodic basis. Thus, a substantial amount of plastic must be used to make the cards, paper must be used to mail the cards to users, and a substantial amount of paper and plastic is eventually thrown away, resulting in waste, degradation of the environment, and a loss of money.

SUMMARY OF THE INVENTION

It is an object of the present invention to provide a universal electronic transaction card ("UET card") which is capable of storing, transmitting and receiving personal and transactional information and thereby replacing plastic cards, which are presently used for the same purpose. In one form of the invention, the universal electronic transaction card of the present invention is a pocket sized device, which includes a microprocessor, random access memory, a display, and input means, and is capable of storing personal information such as the card owner's name, address, date of birth, signature, and likeness, as well as the user's social security number. The UET card is also capable of storing the user's employee number (if applicable), insurance policy number or numbers for various type of insurance, club membership account numbers, credit card company account numbers for a variety of credit card companies, automatic banking numbers for one or more bank accounts, and any other financial or personal transactional information. The UET card is also capable of processing transactional information and communicating with central processing units or computers operated by the providers of services, such as credit card institutions, banks, health care providers, retailers, wholesalers or other providers of goods or services. The UET card is also capable of communicating with personal computers, including those used by retailers (point of sale computers), and personal computers used in other business applications or at home.

In one embodiment of the invention, a UET card is provided for storing, transmitting, and receiving information for a plurality of service institutions. As used herein, the term "service institution" includes any business, service, governmental agency, or other entity, which issues any type of card commonly carried by an individual for the purposes of identification, credit transactions, bank transactions, licensing, registration or similar functions. The information stored, transmitted, or received by the UET card may include personal information of the user of the UET card. It may also include account information for each service institution with which the user has an account. As used herein, the term "account information" includes any identifying designation which identifies the UET card user with a service institution, including but not limited to the user's name, address, phone number, social security number, credit card account numbers, bank account numbers, license numbers, identification numbers, insurance account numbers, medical identification numbers, and the like. The information stored, transmitted, or received by the UET card may also include transactional information for accounts with service institutions in which the UET card user has an account. As used herein, the term "transactional information" includes information relating to one or more individual financial transactions, such as credit card transactions, medical treatment payments, insurance payments, and the like. The transactional information includes various transaction details that may appear on a paper receipt for any given financial transaction, such as a subtotal, a tip, if any, a transaction total, the date and place of the transaction, and the user's signature.

In another embodiment of the invention, the information stored, transmitted, and received by the UET card includes promotional information. As used herein, "promotional information" includes advertisements, electronic facsimiles of coupons, and usage incentives such as "frequent flier miles," cash back rebates, or any of various incentive programs offered by credit card issuers.

In another embodiment of the invention, the information stored, transmitted and received by the UET card includes stored cash value information. As used herein, "stored cash value information" includes information relating to a cash balance which may be stored on the UET card, credits or debits to the cash balance, a traveler's checks balance which may be stored on the UET card, credits or debits to the traveler's check balance and graphical images of various denominations of currency and traveler's checks. In this embodiment, the UET may be used as an electronic equivalent to cash or traveler's checks. Electronic cash or traveler's checks are inherently safer than conventional counterparts, however, due to the security features of the UET.

The UET card comprises housing means adapted to fit in a pocket or a purse which houses inputting means, memory means, communications means, display means, and processing means. Inputting means are provided for inputting information, including personal information for the user, account information for a plurality of service institutions in which the user has an account, and transactional information for each service institution for which account information exists. Memory means are provided for storing the information inputted by the inputting means. Communications means are provided for electronically communicating information stored in the UET card. The UET card includes display means for displaying information for a plurality of service institution accounts, including personal information, account information, and transactional information. In a preferred embodiment the display means comprises a touch-sensitive LCD display. In a preferred embodiment, the UET card is also provided with processing means for processing information, although if required by cost considerations, the processing means could be provided by a personal computer or a communications interface unit (which is described below). Means are also provided for providing and storing electric power and for selectively providing power to the components of the UET card. The UET card also includes security means for preventing unauthorized use of the universal electronic transaction card and for preventing unauthorized access to the information stored in the memory means of the universal electronic transaction card.

In a preferred embodiment, the UET card includes a touch-sensitive display which is large enough to display a visibly perceptible replica of a credit card and a visibly perceptible replica of the user's signature. Menus can be provided on the touch sensitive display to enable the user to select one service institution from a group of service institutions in order to proceed with a transaction using the card. Further, the touch-sensitive display may be provided with multiple levels of menus, including at least one level enabling the user to select from groups of service institutions, and at least one other level enabling the user to select a particular service institution. In addition, a graphic image of a service institution may be displayed when the service institution is selected by a user, along with the user's name and account number. Alternatively, instead of a touch-sensitive display, the UET card may be provided with a pointing device.

The UET card can also be provided with a variety of other menus, which permit the user to review account information for a selected service institution, or a record of transactions with a service institution. In addition, the user's signature can be inputted into the UET card and thereafter displayed for security purposes. The electronic transaction card may further include means for automatically canceling at least one account in the event that a non-authorized user attempts to use the card to conduct an unauthorized transaction with the user's account.

The UET may also include power means for selectively providing power to the display means, the processor means and the communication means. In one such embodiment, the means for providing and storing electric power includes first power means for providing backup power to the memory means and second power means for selectively providing power to the memory means, inputting means, display means, processing means and communications means. In addition, the UET card may further be provided with means for detecting inputting and processing activity and for turning off power to display means and processing means upon detecting no inputting or processing activity for a predetermined time interval.

The present invention also provides for a universal electronic transactions card and communications system ("UET card and communications system") for storing, transmitting, and receiving the type of information discussed above for a plurality of service institutions. The system includes a plurality of UET cards adapted to fit in a pocket or a purse and a plurality of communications interface units ("CIU"). At a minimum, the UET cards must include memory storage devices and means for electronically transmitting information to and from the UET memory. Preferably, the UET cards in this UET card and communication system are also provided with touch-sensitive display means, and processing means. Either the UET card or the CIU device must have display means for displaying information for a plurality of service institution accounts, including personal information, account information, and transactional information; processing means for processing information, including personal information, account information, and transactional information; means for providing and storing electric power and for selectively providing power to the memory means, inputting means, display means, processing means and communications means; and, security means for preventing unauthorized use of the universal electronic transaction card and for preventing unauthorized access to the information stored in the memory means of the universal electronic transaction card.

Thus, in the UET card and communications system, the CIU device may comprise a passive interface between the universal electronics transaction card and a personal computer. In that event, the UET card may be equipped with memory, processing means, touch-sensitive display means, and means for interfacing with the CIU device. Information may be communicated from the UET card through the CIU device to the personal computer, where it may be processed by the computer to produce electronic reports in the nature of monthly statements now received from service institutions. In addition, modem communications with a central system may be done by the personal computer. Alternatively, in the UET card and communications system, the CIU device may comprise a passive interface with the universal electronics transactions card and a modem. Or, the CIU may have more features, including a passive interface with the universal electronics transactions card, a modem, means for processing information, means for storing information, input means for entering information, and display means for displaying information.

The invention also includes an electronic transaction system which includes a plurality of UET cards, CIU devices, point of transactions systems, and an institutional system. The point of transactions system includes means for inputting and storing transactional information; means for electronically communicating with the UET card to receive account information; means for electronically communicating the account information and transactional information to an institutional system; and means for electronically communicating transactional information to the personal electronic transaction card. The communications between the UET card and the point of transactions system may be done through the CIU device. The institutional system includes means for creating account numbers; means for assigning and authorizing account numbers; means for electronically communicating an authorized account number to a universal electronic transaction card; means for receiving and storing personal information for each authorized account number; means for communicating with a personal electronic transaction card to authorize account transactions, and means for receiving and storing information relating to account transactions. Communications systems are provided to enable communications between the universal electronic transaction card and point of transactions system and between the point of transactions system and the institutional system, including card interfacing means for interfacing between the transactional provider system and the universal electronic transaction card to exchange electronic information; and communications means for communicating with the institutional system.

In one application of this invention, a health care management system is provided in which UET cards are used for inputting, storing, processing, and transmitting personal information, including personal medical history, account information, and transactional information. At least one central health care information processing system is provided, and it includes means for creating, assigning and storing patient and health care provider accounts; means for electronically communicating account information to a universal electronic transaction card; means for receiving and storing personal information for each authorized account number; means for communicating with a universal electronic transaction card to authorize account transactions, means for receiving and storing information relating to account transactions; and means for storing and communicating medical histories. In this system, the UET card is used by a patient when the patient visits the health care provider. Health care providers may include doctors, hospitals, laboratories, pharmacies, out patient clinics, and the like. Health care providers use a health care provider processing system, which includes means or electronically communicating with the central health care information processing system; means for electronically communicating with the UET card; and memory means for storing patient information. Communications systems are also provided for providing communications between the universal electronic transaction card, the central health care information processing system, and the health care provider processing system.

When a patient visits a health care provider, the patient's UET card is interfaced with the health care provider processing system, which in turn may communicate with the central health care processing system. All pertinent information concerning the patient's health is then instantly available to the health care provider, including the patient's medical history, insurance coverage, and the like. After the patient is treated, or is provided with a medical service, billing is automatically done by the system, and all pertinent information concerning the billing is electronically transmitted to the patient's UET card and also to the appropriate service institution.

This invention also includes a method of conducting an electronic credit transaction using a service institution account which includes the steps of (1) selecting from a UET card a service institution account from a group of service institution accounts; (2) establishing an electronic communication between the universal electronic transaction card, a point of transaction system and a service institution system; (3) transmitting from the universal electronic transactions card to the point of transaction system the account information for the selected service institution account; (4) transmitting from the point transaction system to the service institution system transactional information for the credit transaction and the service institution account; (5) in the service institution system, screening the service account and transactional information to determine whether the account is valid and whether the credit transaction is within predetermined credit limits for that account; and (6) for valid accounts and credit transactions within predetermined limits, transmitting an authorization for the credit transaction to the point of transaction system, storing the transactional information for the credit transaction in the service institution system with respect to the service institution account, and transmitting the transactional information for the credit transaction to the universal electronic transaction card and storing the transactional information for the credit transaction in the universal electronic transaction card with respect to the service institution account.

This invention also includes a method of issuing an account by a service institution to a user of a universal electronic transaction card to authorize the user to use the universal electronic transaction card for the account. The method includes the steps of (1) obtaining predetermined information from the user as required by the service institution; (2) issuing account information for the user, including an account number; and (3) electronically transmitting to the user's universal electronic transaction card predetermined account information for the service institution account and predetermined information about the service institution and the account to be displayed by the universal electronic transaction card when the universal electronic transaction card is used to conduct a credit transaction for such account. Among other things, the predetermined information may include the name of the service institution account service and a graphic image of the service institution's account service logo.

This invention also includes a method of transferring account information and accumulated transactional information for a plurality of credit transactions for a service institution account from a UET card to a personal computer. The method comprises the steps of establishing an electronic communication between a personal computer and a UET card; selecting at least one service institution account; selecting from the at least one service institution account credit transactions for such account which were transacted in a predetermined period of time; and, transmitting from the universal electronic transaction card the selected credit transactions to storage means in a personal computer. The selected credit transactions may thereafter be displayed on the personal computer in the form of a monthly statement of the type normally provided on paper by the service institution.

The invention also includes a method of using a UET card as a remote terminal for a service institution system. The method includes the steps of selecting a previously authorized service institution account from the universal electronic transaction card; establishing an electronic communication between a personal computer and the service institution system for such service institution account; transmitting to the service institution system from the universal electronic transaction card identifying information for the user and for the service institution account; comparing the identifying information with authorization information in the service institution account to determine if the identifying information is valid; and, for valid identifying information, communicating selected account and transaction information between the universal electronic transaction card and the service information system, responsive to commands communicated from the universal electronic transaction card to the service information system. The selected transactional information may thereafter displayed on the universal electronic transaction card in the form of a monthly statement of the type normally provided on paper by the service institution.

There are several advantages to the present invention. With respect to credit card transactions, the UET card of the present invention may be used to store in memory each credit card or bank transaction for which it is used. Those transactions may be displayed on the display of the UET card. Alternatively, the contents of memory may be electronically transferred to a personal computer for use in any one of a number of commercially available personal accounting programs, such as the program commercially sold under the name "QUICKEN". Alternatively, the information could be used with spreadsheet programs, such as LOTUS or EXCEL. Alternatively, the UET card may be provided with a disk containing a program that may be used on a personal computer to display and print the information. Or, for those card users who might not own a personal computer, a printer may be provided to interface with the card and to print the record of the desired transaction or transactions.

Given the capability of retaining an electronic record of transactions, the user of the UET card would have no need for a paper record of the transaction, and the paper receipt at the point of sale could be eliminated. Further, since the information concerning each credit card transaction would be recorded in the memory of the UET card at the time of the transaction, there would be no need for the generation of a monthly statement from the credit card provider to the UET card owner. In fact, the UET card owner could eliminate all paper transactions and bills by using an electronic method of paying the credit card provider by any one of the methods that are currently available.

There are also several advantages that may be realized by the application of the present invention to the health care industry. A patient's insurance information, and key medical history information may be maintained in the memory of the UET card. Alternatively, or in addition, a patient's complete medical history may be maintained in a universal database, accessible over a health care data network similar to the network presently known as the INTERNET. Thus, every time a patient using a UET card would visit a doctor, or a hospital, or an out patient clinic, or a pharmacy, the patient's medical history would be available so that the health care provider or pharmacist would have instant access to information that might prevent the prescribing of drugs or other treatment which would not be tolerated by the patient, because of allergic reactions or other contraindications.

The foregoing advantages are some examples of the advantages provided by the present invention, and are not intended to be exhaustive. Specific examples of the implementation of the invention are shown in the drawings and are discussed herein. Those examples are intended provide examples of the invention, not to limit it. The scope of the invention is expressed in the claims.

DESCRIPTION OF THE DRAWINGS

FIG. 18 illustrates commands that may be used on the UET card of the present invention.

FIG. 26 illustrates the use of an alphanumeric keyboard on the touch sensitive display of the UET card.

FIG. 27 illustrates additional features that may be added to the UET card of the present invention.

FIG. 28 outlines a "to do" list on the UET card of the present invention.

DETAILED DESCRIPTION

Figure 1:
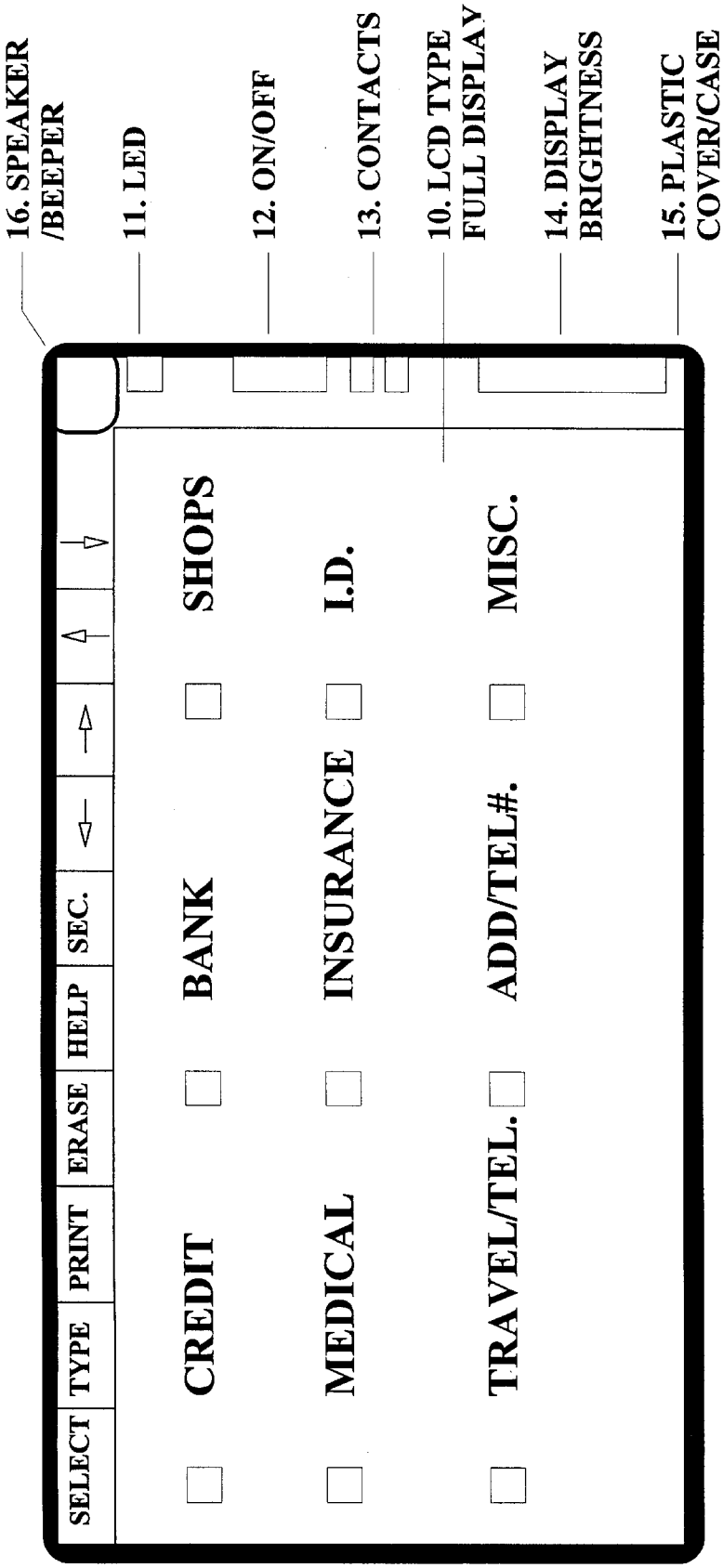
FIG. 1 is a front view of one embodiment of a universal electronic transaction card in accordance with the present invention.

The embodiment of the Universal Electronic Transaction (UET) Card shown in FIG. 1 consists of a large full scale liquid crystal display with touch-memory screen 10, a LED light emitting diode to indicate on/off status 11, an on/off switch 12, metal contacts 13 to read/write to and from the memory and to charge the battery through an external unit, such as a communications interface unit, a slide type control to manage display brightness 11, plastic cover and enclosure 15, speaker or beeper 16 to activate an audible alarm during low battery or a reminder signal and associated electronics hardware and software to store and analyze personal, account, credit, and transactional information. The size of the UET card may be around 3½"×2 ½", which is similar to the normal plastic credit card in use today. It is designed to be carried in the wallet and/or packets.

In the preferred embodiment discussed herein, the user may enter information into the memory of the UET card by touching selected parts of the touch-sensitive display. Alternatively, if the display is not touch-sensitive, the user may input information by using a mouse or other pointing device, which may be in the form of a trackball built into the UET card.

Figure 2:
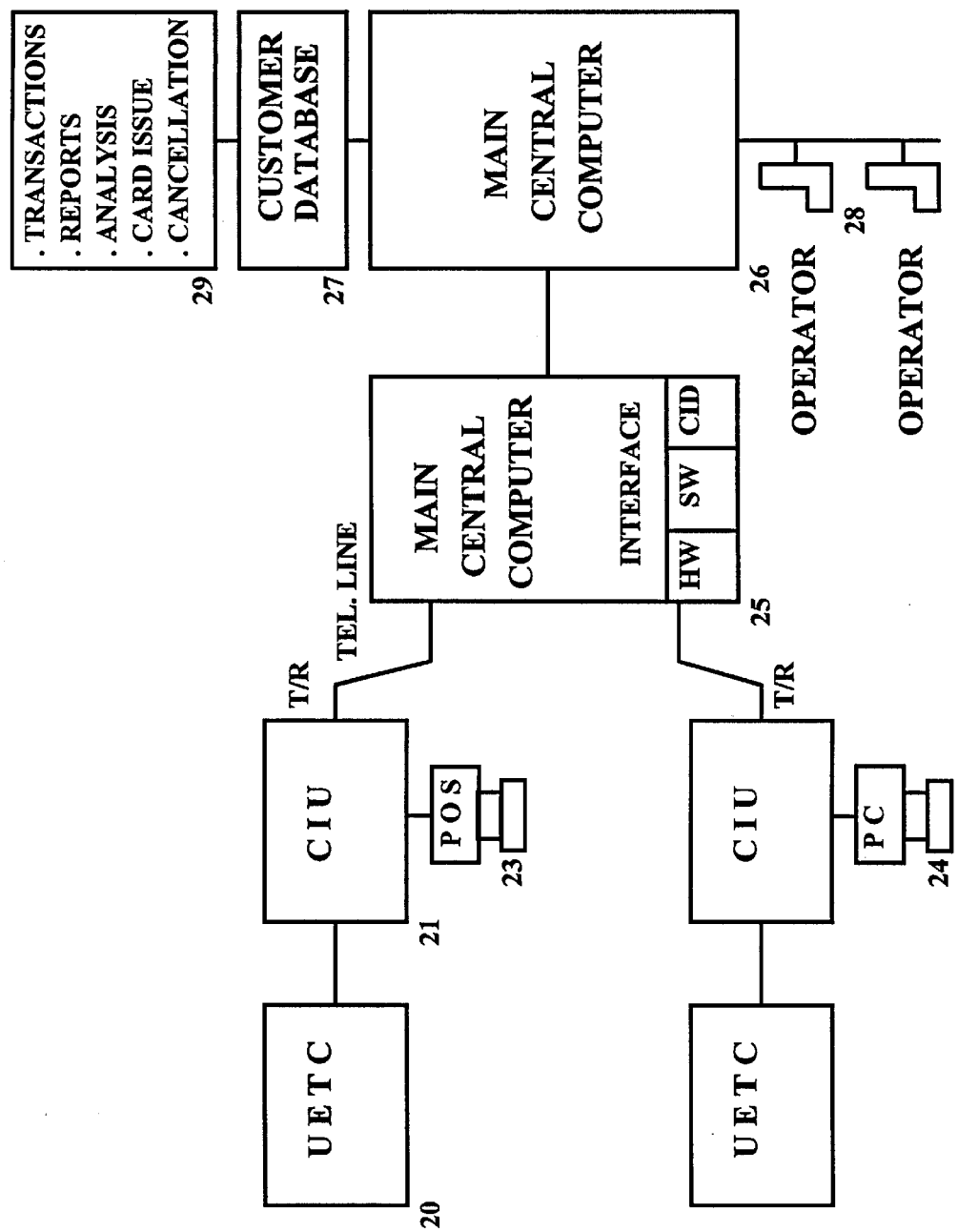
FIG. 2 is a block diagram illustrating one embodiment of a universal electronic transaction card system in accordance with the present invention.

FIG. 2 shows an embodiment of the overall UET card system configuration. It includes a communication interface unit ("CIU") 21, which interfaces with the UET card either through physical metallic contact—preferred for the touch memory devices—or infra red or radio frequency based wireless transmit and receive units. The CIU includes means for receiving data from the UET card, such as metal contacts to connect to the metal contacts 13 of the UET card, or infrared or radio frequency based wireless systems, depending on the system used by the UET card. In addition, the CIU is provided with memory means for storing data, such as random access memory devices (RAM), means for processing data, such as a microprocessor, and means for directly communicating with the point of sales ("POS") and home or office personal computer ("PC"), such as serial or parallel ports. The CIU is provided with a modem or other suitable means for telecommunicating with remote computers and data base facilities for credit verification, card issuing, bill payments, etc. Some of the features offered by the CIU can also be incorporated directly into UET card provided the size of the card can remain small enough to carry it in the pockets.

The POS computer 23 interfaces directly with the CIU to read/write information to and from the UET card and communicate with the main central computer of the credit card or bank card company for customer data base, credit verification, etc. The POS computer also writes transaction information directly into the UET card thereby eliminating need for paper receipts. The POS computer may vary in size, shape and applications, and as a result, the CIU is provided with software which will adapt to a variety of POS computers in use today or which may be used in the future. Software for communicating between computers is readily available in the marketplace today. Alternatively, special software may be written to enable the CIU to communicate with the POS computer.

The home PC 24 interfaces with the UET card to perform transactional analysis needed for tax review, summary, or budgeting purposes. Software for interfacing between the home PC and the UET card for reading information from the card is available, so long as conventional memory components are used, or can be specially written. Software enabling the PC to dial directly to the main central computer used by a service institution with whom the user of the UET card has an account is readily available. For the purpose of electronic communications with the service institution, the PC must be equipped with a modem.

At the main central computer a special interface 25 is required with appropriate hardware to concentrate multiple telephone lines, and software to keep the existing methodology and formats used by the credit card and banking industries. The interface also provides caller identification feature normally available from the local telephone companies to add security. Through the caller identification feature, it is possible to identify the location of the originating call for every transaction, such that along with each transaction a telephone number can be tagged to trace misuse of the UET card. This interface 25 is very similar to the existing interfaces except for the unique software and the added caller identification feature.

The main central computer 26 is used by all the credit card issuing companies or other service providers for management and monitoring. The computer includes customer data base 27, operator positions 28 for customer services, and facilities to store and process transactions, reports, analysis, account authorization, card issuance and cancellation, etc.

The UET card may be configured with sufficient memory to store all transactions electronically, so as to eliminate or reduce the need for paper receipts. The transactions thus stored in the UET card may be downloaded into another computer, such as the user's home personal computer, or the main computer. The main computer may also be provided with the capability of analyzing transactions, generating reports and issuing new cards electronically by transmitting an electronic image of the card after caller identification and verification. This electronic image may include the name, credit card number, date of issue, date of expiration, credit limits, and a graphic image of the card, along with a variety of coded security information unique to the credit card issuing company and the card holder to eliminate fraud and misuse.

It should be emphasized that the UET card is capable of interfacing with a variety of mainframe computers for special applications such as medical cards, drivers license identification cards, etc. The transactions for which the UET card is used take place electronically in real time, including issuing a card. The transactions are recorded electronically and do not need paper receipts either at the customer end or at the credit card company end. It is also possible to provide on line analysis service from the main central computer to the UET card holder for credit verification, transaction analysis, billing, payments, etc.

Figure 3:
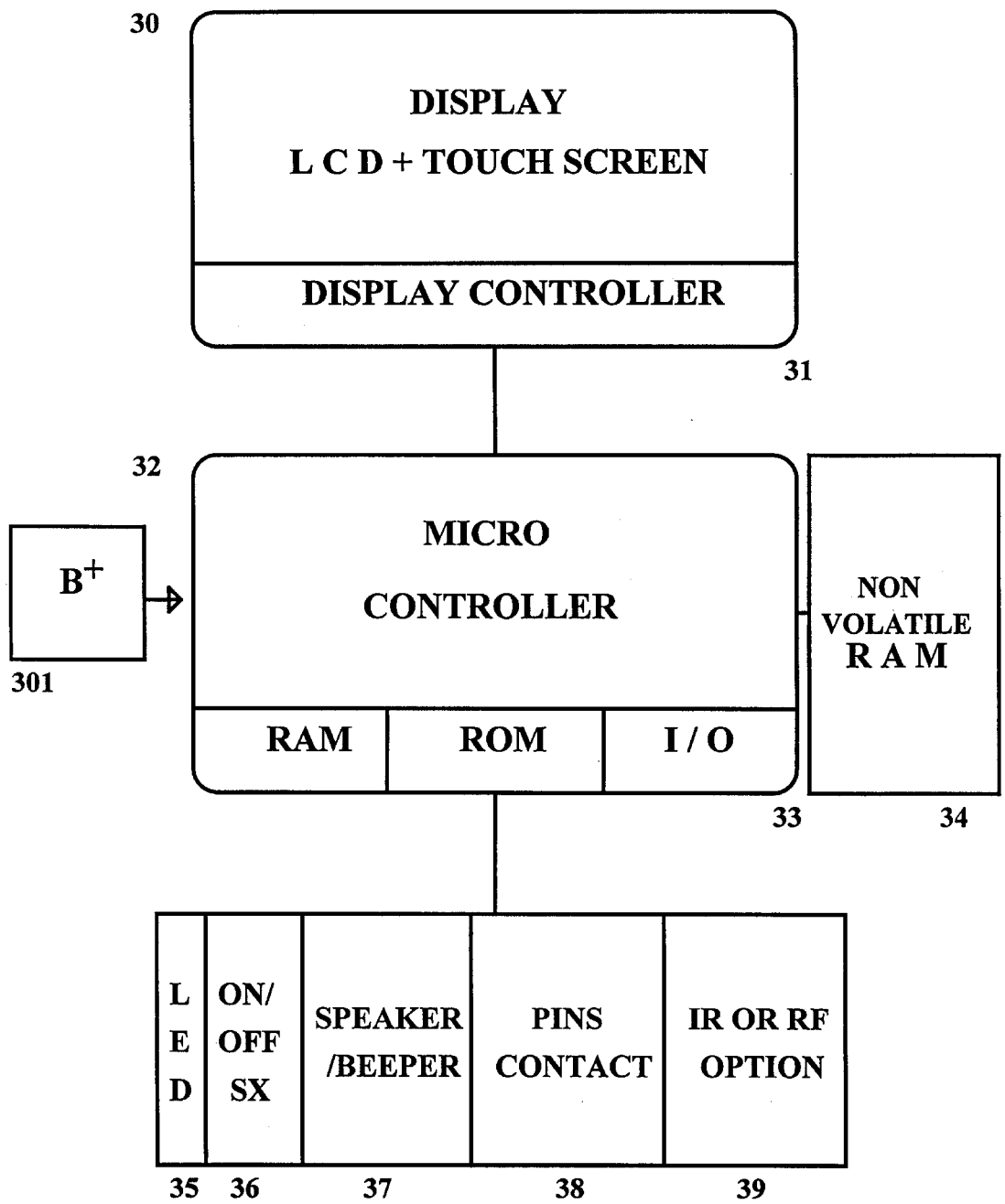
FIG. 3 is a block diagram of one embodiment of the UET card of the present invention.

FIG. 3 is a block diagram of the major components of the UET card of the present invention. In the preferred embodiment, the UET card includes a full scale LCD & touch screen display 30, although the display can be a smaller size, so long as it is large enough for the messages displayed on it to be readable by a user and so long as it is large enough to enable a user to operate the touch controls discussed herein. The UET card also includes an associated display controller 31, a micro controller along with RAM/ROM/and Input/Output port management 33, a non-volatile RAM 34 and or touch memories with direct contact to connect to the CIU, a light emitting diode 35 to indicate the status of on/off switch 36, a speaker/beeper 37, pin contacts 38 to connect to the memory and to charge the battery, infrared or radio frequency option to communicate and, a built in rechargeable or ordinary batteries 301 to power all electronics for the card.

The UET card is an active device with a display which is large enough for the user to view information relating to the "credit card" to be used in a transaction, the details of the transaction, and the other information described herein. The memory must be of sufficient size to store a predetermined number of different cards and transactions. The main purpose of the UET card is to consolidate variety of plastic cards in one and to eliminate paper transactions by storing all transactions in the card memory, which can be down loaded to the home PC.

Figure 4:
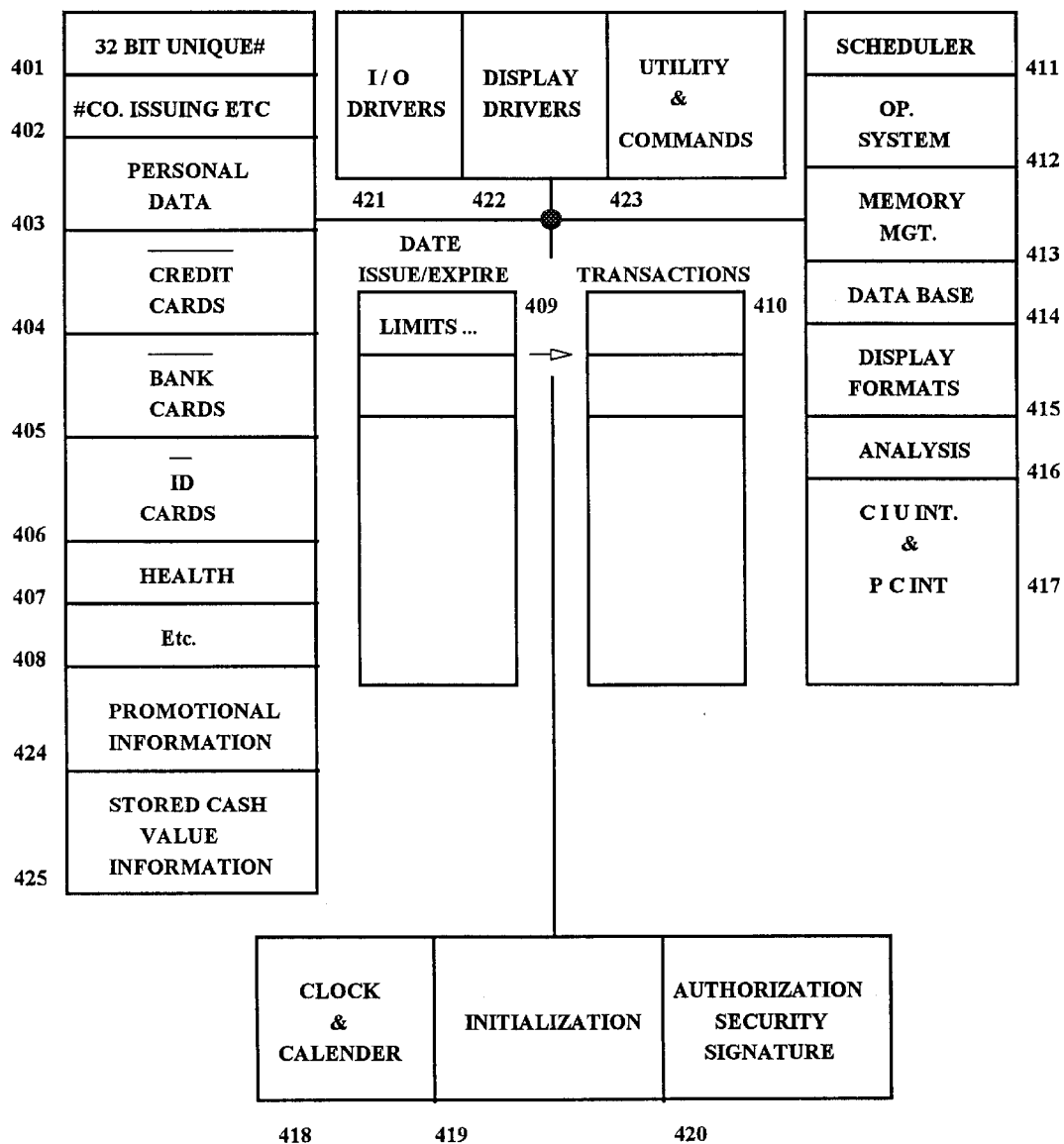
FIG. 4 is a functional diagram of the software blocks used in one embodiment of the UET card.

FIG. 4 is a diagram of the major software blocks which may be used in the UET card. The software blocks include a database which may include, for example a 32 bit-non erasable unique number 401 assigned to each UET card for security; a primary credit card issuing company or service institution number 402 which includes information about service institution, such as the name, address, telephone number, etc.; personal data 403 such as name, address, telephone number, fax number, office address, phone number, height, weight, birth date, social security number, blood type, marriage status, and other appropriate information; credit card account information 404, such as American Express, Visa, Diners Club, containing data similar to that stored in present plastic card magnetic strips along with the visible information on the cards, bank cards 405; ID cards 406, including photographs of the user, fingerprints or other forms of identification; health cards 407; or any other cards 408, such as, travel, car rental, specialty shop, or restaurant cards. The data base may also include promotional information, 424, such as airline frequent flier data and stored cash value information 425, including a stored cash or traveller's check balance.

It should be emphasized that the primary credit card issuing company provides the first hardware/software and all the necessary interfaces to the customer. Thereafter secondary card issuing companies will issue new cards by writing electronic prints by dialing in to the card along with appropriate customer and card issuing company information.

Corresponding to each card, a data area 409 is provided for transient information related to the date of issue, date of expire, credit limit, etc. This can be charged periodically by the card issuing company. Also corresponding to each card, a transaction memory area 410 is provided to store all transaction receipts in electronic form to eliminate or reduce paper receipts. The transactions can be down loaded to a home/office PC. In addition, transactions are also stored in the main central computer of the card company.

The UET card software also includes an operating system 412, memory management 413, database management 414, display formats and associated management 415, analysis algorithms and procedures 416, and a CIU and PC interface 417. In addition, the UET card software may also include a scheduler 411, and other utilities, as desired.

The UET card software also includes modules for I/O drivers 421, display drivers 422, utility & command management 423, clock and calendar 418, initialization 419, and authorization/security and signature management 420.

Initially, when the on/off switch is turned on, the I/O driver detects it and turns on the display and prepares the UET card for use. Thereafter the main display provides options to be selected by the card user through a touch screen. A variety of options are available and UET card can be programmed for special applications as desired. All the individual software blocks outlined here are standard and familiar to any one knowledgeable in the software field.

Figure 5:
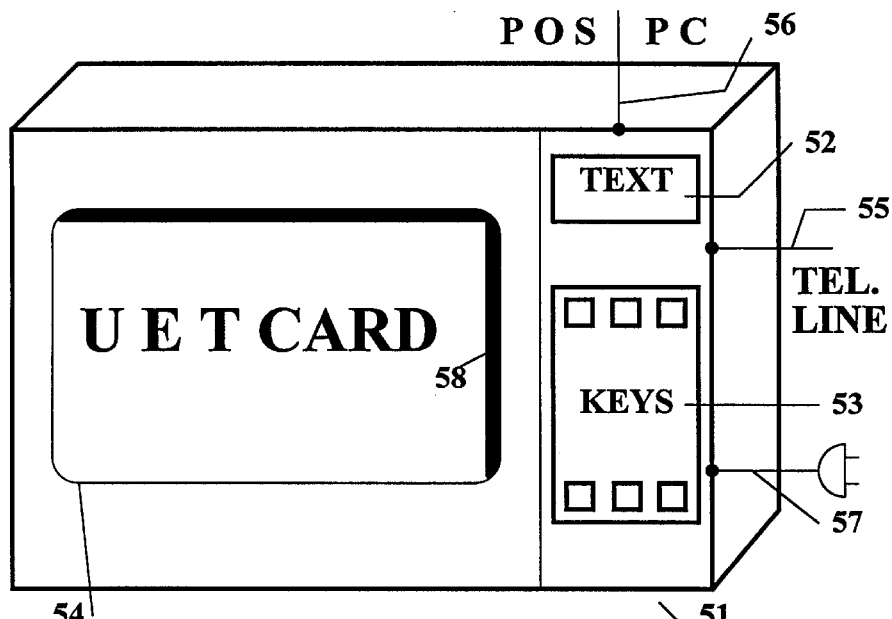
FIG. 5 is a front view of one embodiment of a communication interface unit of the present invention.

FIG. 5 shows the CIU hardware 51. The CIU is used for interconnecting UET card to PC/POS and the main central computer through normal telephone lines. As shown in FIG. 5, the CIU includes a display for text 52 which may be a liquid crystal display a cathode ray tube, or some other form of display. It also includes a key pad 53 for dialing and start/stop and special functions, a physical connector 58 to communicate with the UET card 54, a telephone line interface 55, a PC/POS interface 56, and a power line connector 57.

Figure 6:
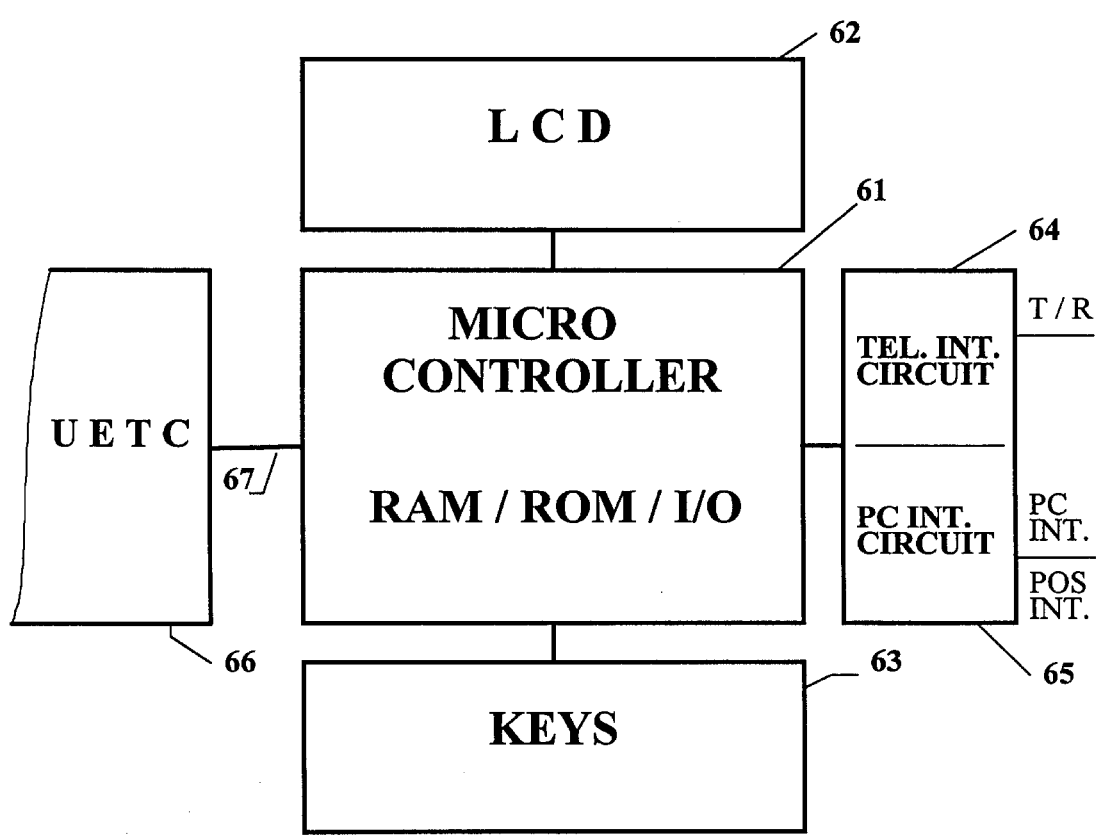
FIG. 6 is a block diagram of one of the components of the communication interface unit of the present invention.

FIG. 6 is the block diagram of the CIU. The CIU comprises a microprocessor 61, a display 62, which may be a liquid crystal display or other suitable display, keys 63, a telephone interface 64, a PC/POS interface 65, a UET card position 66, and a UET card contact 67.

Figure 7:
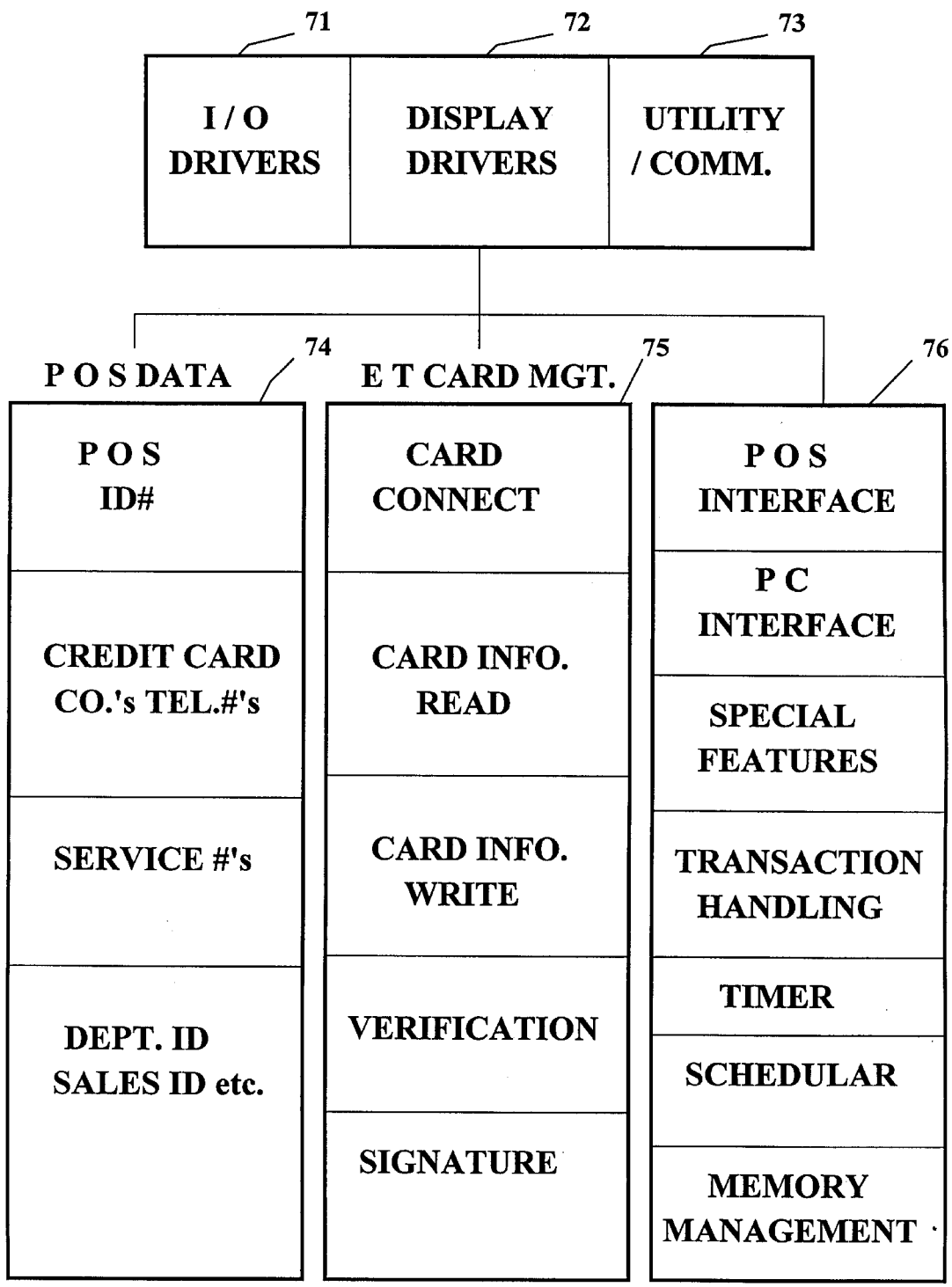
FIG. 7 is a block diagram of the software blocks used in one embodiment of the communication interface unit of the present invention.

The software for the CIU is shown in FIG. 7. It includes I/O drivers 71, display drivers 72, utility/command management software 73, and a POS database 74 to include one or more POS ID numbers, credit card company numbers, service numbers, and department identifications or sales identifications, or the like. It also includes UET card management software 75, and may also include other software 76.

When a user of a UET card wishes to use the UET card for a transaction, the card is connected to the CIU unit. When the metal contacts of the UET card are connected to the corresponding contacts or port of the CIU, the CIU software recognizes the UET card contact and prepares itself to read information from the UET card. It also dials the main computer center for verification and interfaces with POS computer. The CIU unit may include software capable of displaying signatures or other types of verification/identification such as photographs, finger prints or voice prints.

The other software 76 for the CIU unit may include an interface for a point of sales computer or for a home computer. It may also include special features, transaction handling, a timer/scheduler, and memory management software.

Figure 8A:
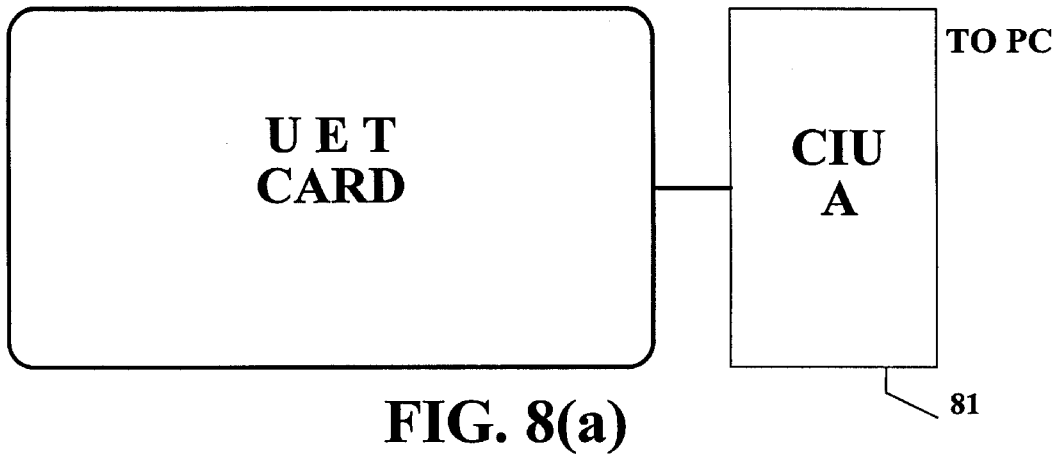
FIG. 8 is a diagram illustrating three different versions of a communication interface unit used in the present invention.
Figure 8B:
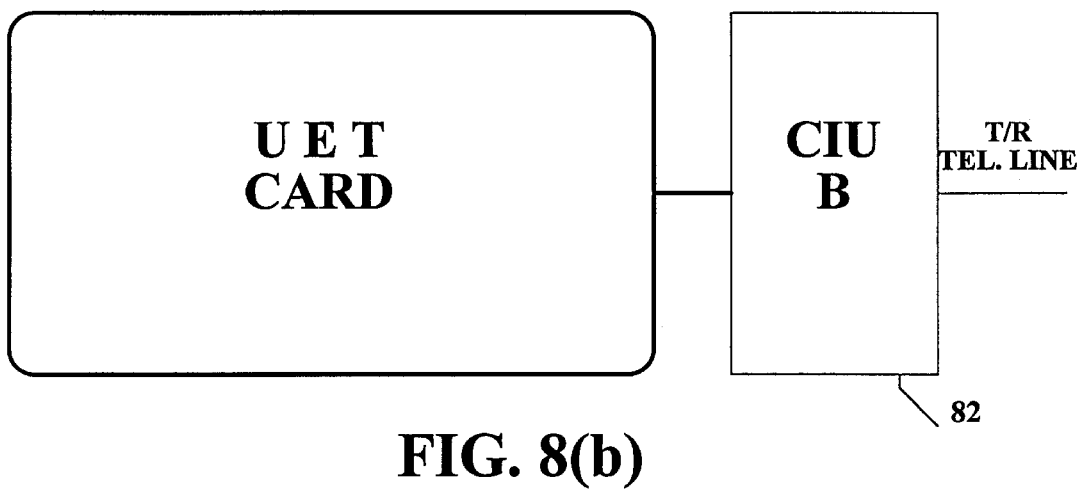
Figure 8C:
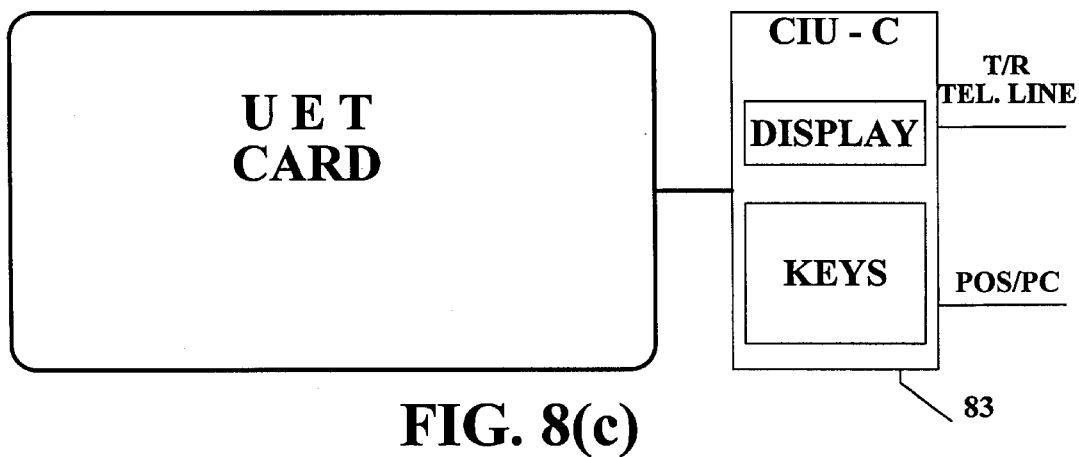

FIG. 8 illustrates three different versions of the CIU. CIU A is a passive interface between the UET card and a personal computer. CIU A includes metal contacts for connecting with the UET card and a serial port or a parallel port or other means for communicating with a home/office PC. CIU A is a passive device, which does not include any processing capability, memory, or software which may otherwise be present in a CIU. Those functions are incorporated in the personal computer to avoid duplication and reduce cost. In this configuration, the PC is provided with communications software and a modem so that it is capable of dialing to the main computer center.

If the UET card user does not have access to PC at home or office, but would like to use the main computer for analysis, he/she may use CIU B shown in 82. CIU B may include only a modem and metal contacts or other means for communicating with a UET card. In that case, the software for operating the modem in order to communicate with the main computer is present in the UET card.

CIU C 83, which includes a microprocessor, memory, a keypad or keyboard, a modem, and an interface for the UET card, and an interface for a personal computer, is necessary only when all the facilities are required in one unit to dial remote main central computer and inter connect with PC and POS.

CIU A, CIU B, and CIU C may include a metallic contact for connecting the CIU to the battery 301 of the UET card. In such an embodiment, the battery 301 is recharged each time the UET card is connected to a CIU for a transaction. This embodiment provides for convenient recharging of the battery 301, and substantially eliminates the need to replace a conventional battery during normal use.

Figure 9:
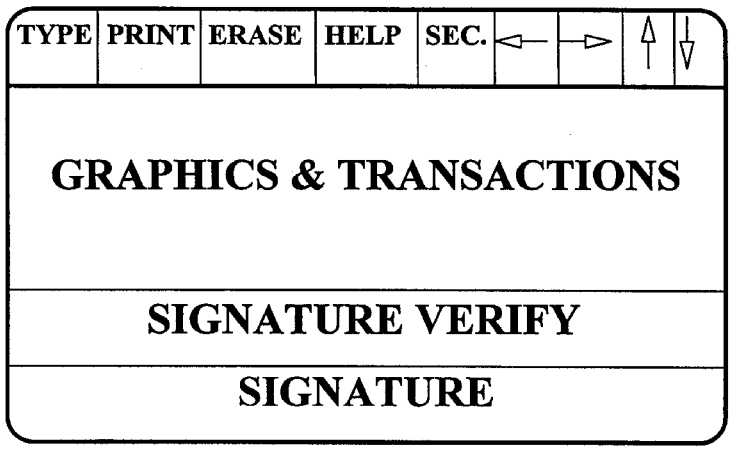
FIG. 9 illustrates one embodiment of the display of the UET card of the present invention.

FIG. 9 illustrates various display areas for the UET card. At the top or at the bottom of the display, various commands may appear, such as: "type", "print", "erase", "security", "shift", etc. The remaining part of the display is available for transaction storage display and analysis. A specific area is assigned for the original signature for the permanent record to be used thereafter for identification purposes. In the same area, the customer is requested to sign during a sales transaction, if the signature is used for identification, as opposed to a photograph or fingerprints or a voice print. The original signature sample is used for verification during a sales transaction. It is also possible to display basic card information such as the name, the card number, the date of issue, the date of expiration, etc., in the form of a bar code pattern to be read by a bar code reader in a predetermined area.

Figure 10:
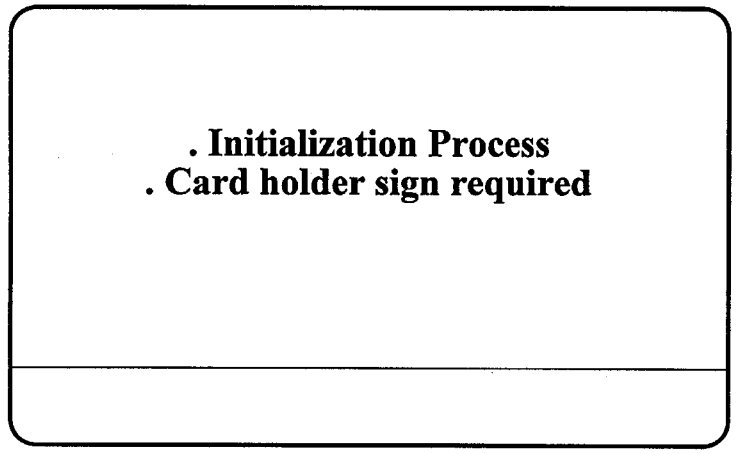
FIG. 10 illustrates a signature made by a user on the display of the UET card of the present invention.

As shown in FIG. 10, during initialization, the card holder is requested to sign in the designated area. This signature becomes a permanent record similar to the one used in the present day plastic cards and is used for visual verification for identification and security. Once signed the signature is stored in a memory location from which it can not be erased by the user. It is called automatically for visual display to verify signature during normal sales transaction.

Figure 11:
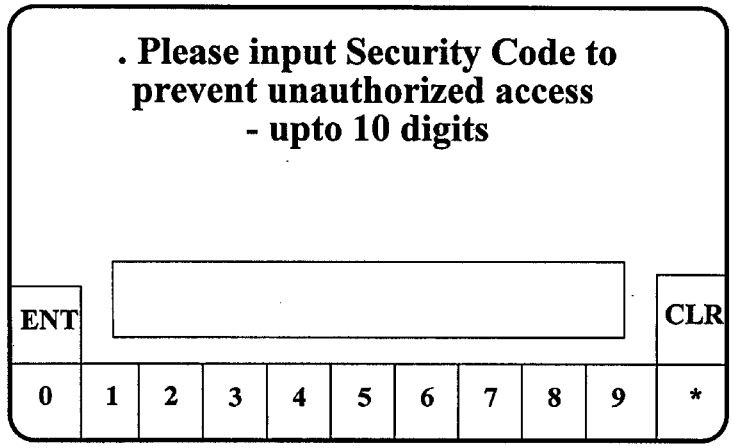
FIG. 11 illustrates a manner of inputting a security code on the UET card of the present invention.

As shown in FIG. 11, a variety of security mechanisms can be built into the UET card to avoid access to confidential information as well to avoid fraud. During initialization the user is requested to select a unique authorization code which may be up to 10 digits. The user-programmed authorization code is intended to be maintained by the user in confidence, much like PIN numbers used in connection with ATM cards. Whenever desired, access to information stored in the card or the ability to use the card can be blocked, unless the proper authorization code is entered. Once the UET card is initialized with a signature and an authorization code it is ready for normal use.

Figure 12:
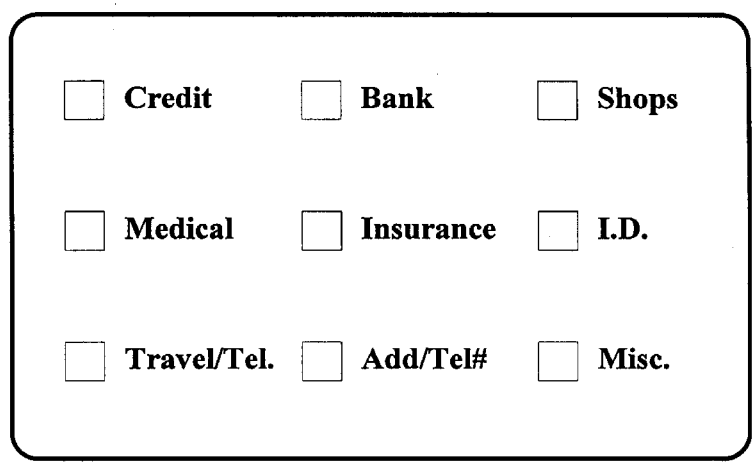
FIG. 12 illustrates a menu for selecting from groups of service institution transactions.
Figure 13:
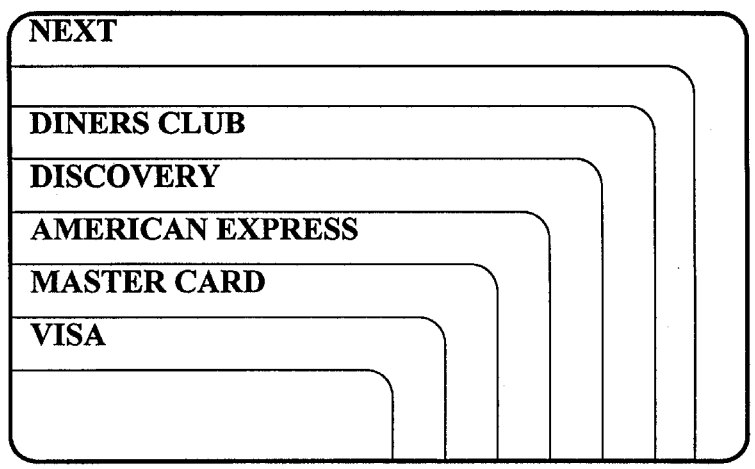
FIG. 13 illustrates a menu for selecting from credit card transactions after selection of credit from the menu shown in FIG. 12.
Figure 14:
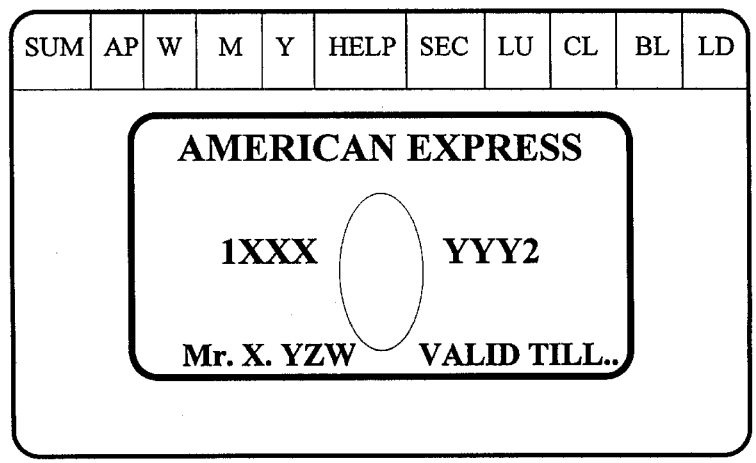
FIG. 14 illustrates a menu for user commands for a credit card transaction for the UET card of the present invention.

When several credit card or service institutions have activated a UET card, a display such as the display in FIG. 12 will appear on the card. This allows user to select any of the card type options for use. For example, the user can select by touching box next to the 'credit' on the screen, all the credit cards available. This is shown in FIG. 13. By touching the area for the American Express card on the touch-sensitive display, for example, the user can see a graphic image of the American Express Card with appropriate user commands as shown in FIG. 14. Through these user commands the card holder can have access to the information related to account summary (AS), account payable (AP), weekly (W), monthly (M), yearly (Y) details. The card holder can also ask for help (H), security (S), last use (LU) credit limit (CL), balance (BL), and load PC (LP). Various other utilities and command can be designed to suit customer and credit card company requirements.

Figure 15:
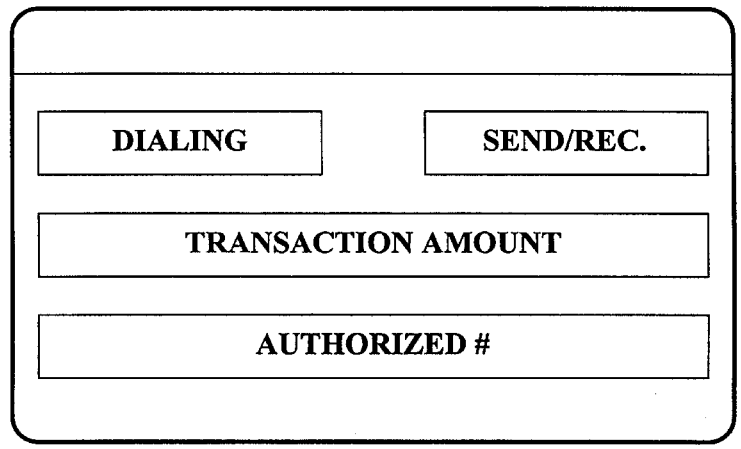
FIG. 15 illustrates a status display on the UET card of the present invention during a transaction.
Figure 16:
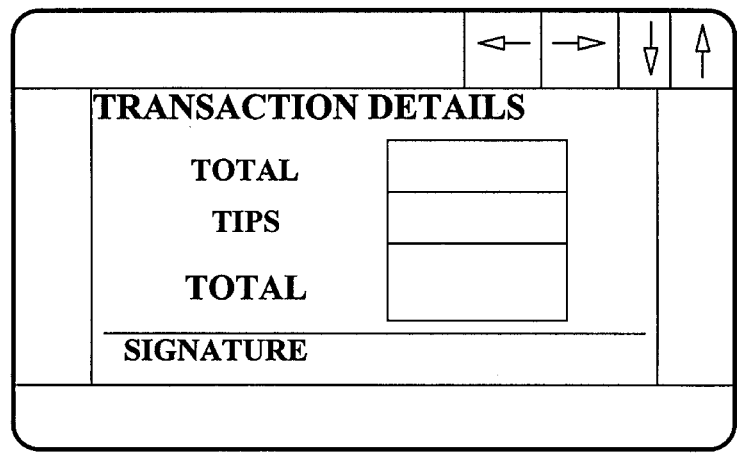
FIG. 16 illustrates another status display on the UET card of the present invention during a transaction.
Figure 17:
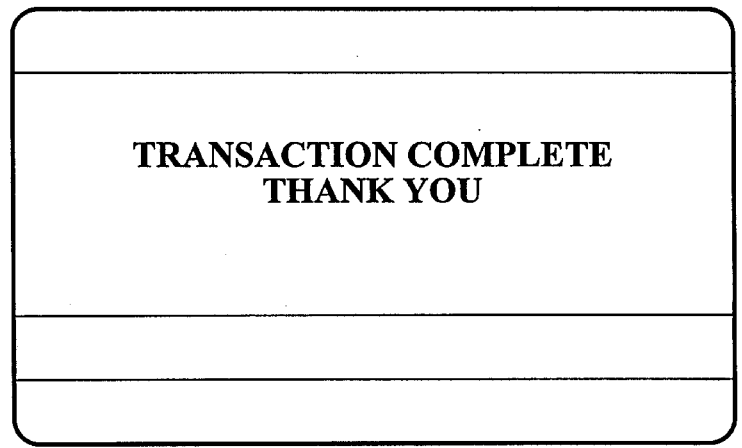
FIG. 17 illustrates a status display upon completion of a transaction.

FIG. 15 displays the status on the UET card during a sales transaction, when the UET card is connected through the CIU to a point of sales terminal. The progress of the dialing process to the main computer, in the form of send/receive etc., is displayed accordingly. Once the point of sales terminal is connected to the main computer, the salesperson can input transaction amount for a credit check and authorization. After proper verification at the main central computer, the authorization will appear on the display of the UET card and/or the point of sales computer. The point of sales computer will download and display the transaction details, as shown in FIG. 16, and transmit the transaction information into the memory of the UET card, on which the transaction information may be displayed for visual verification by the customer. If necessary, such as in a restaurant, the customer can add a gratuity at this stage by using the 0 to 9 keys on the touch-screen display and appropriate commands. Thereafter, the POS salesperson may request the customer to sign the bill on the display in designated area. Once the card holder signs, the customer's original signature, which was stored in memory when the UET card was activated, will appear on the display of the UET card and/or the display of the point of sales computer for visual verification. This would essentially complete normal transaction, as shown in FIG. 17.

A sample of typical commands for the UET card is shown in FIG. 18. Because of the software flexibility, a variety of commands can be developed to changing customer needs. Each set of commands are associated with the display on hand. The commands are required to guide UET card user to process transactions and help analyze transaction details, history, and patterns.

Figure 19:
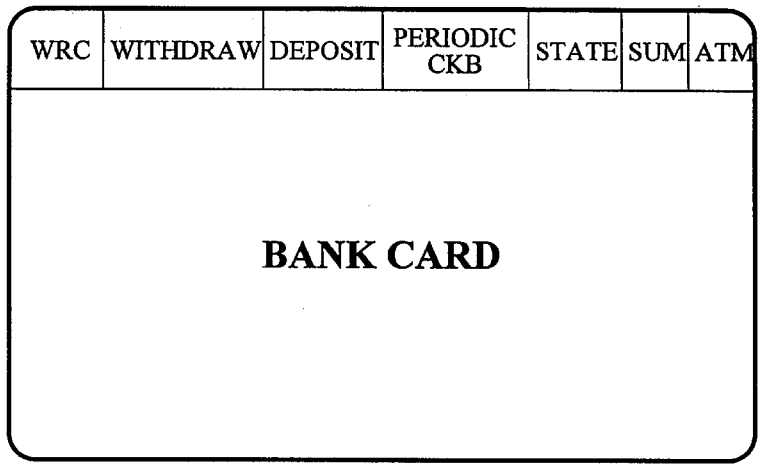
FIG. 19 illustrates an ATM bank "card" as it would be used on the UET card of the present invention.

FIG. 19 shows a typical bank card through which with appropriate interface the card holder can use ATM and perform bank transactions directly with the bank computer with built in security. These transactions may include features such as, withdraw, deposit, write check (WRC), write periodic checks, pay home loans, utility bills, etc., or request monthly statement, account summary, etc. All of the information required for a checking account or ATM transaction is included in the account information for the bank which has issued the bank card authorization to the UET card holder.

Figure 20:
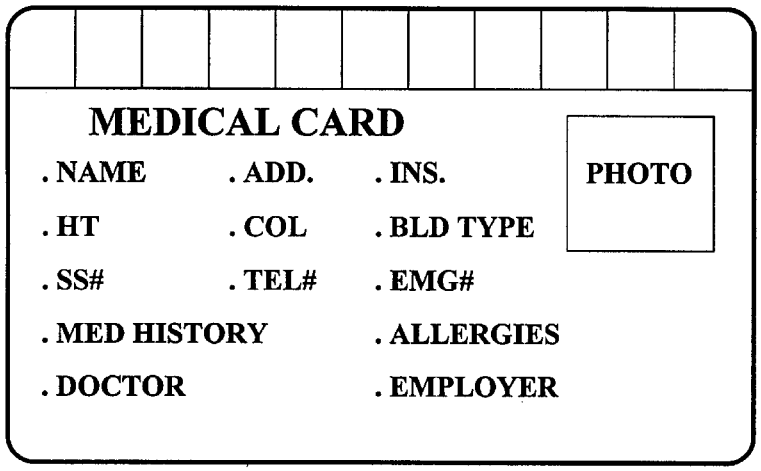
FIG. 20 illustrates a medical "card" as it would be used on the UET card of the present invention.
Figure 21:
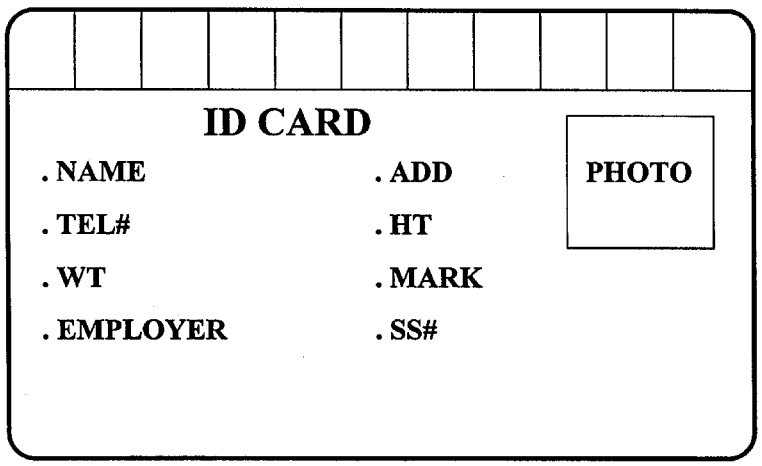
FIG. 21 illustrates an ID "card" as it would be used on the UET card of the present invention.
Figure 22:
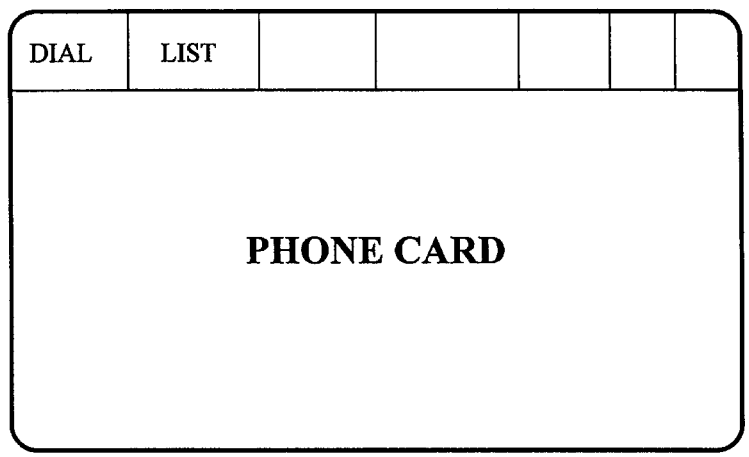
FIG. 22 illustrates a phone "card" as it would be used on the UET card of the present invention.
Figure 23:
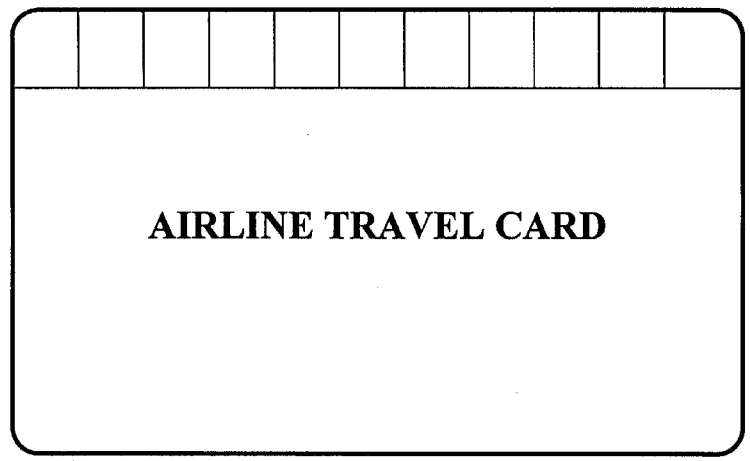
FIG. 23 illustrates an airline "card" as it would be used on the UET card of the present invention.
Figure 24:
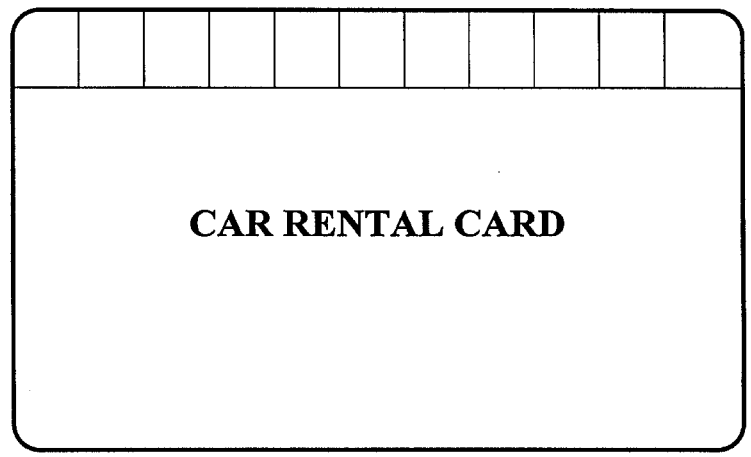
FIG. 24 illustrates a car rental "card" as it would be used on the UET card of the present invention.
Figure 25:
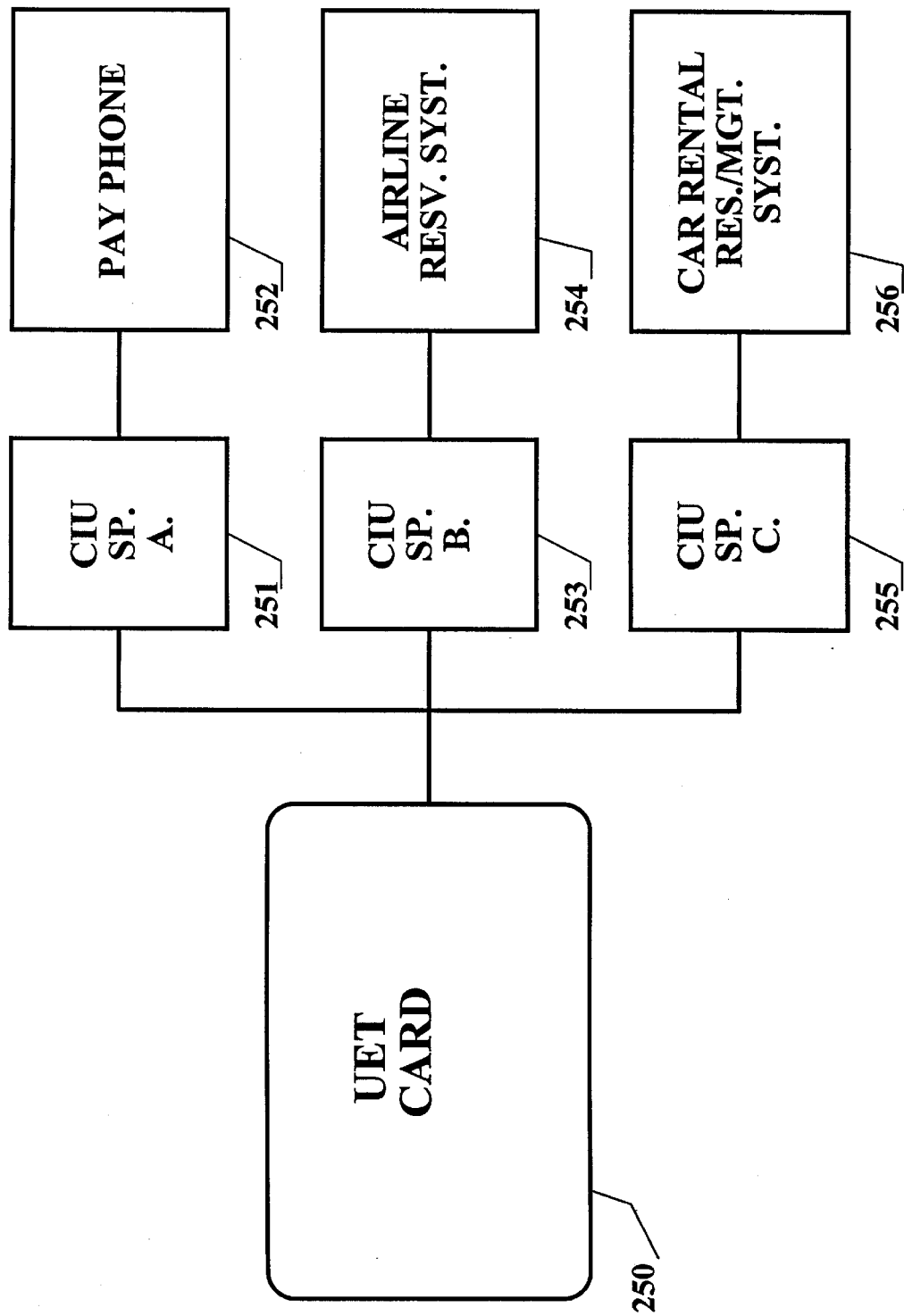
FIG. 25 illustrates special interfaces with the communications interface unit that may be used to handle different protocols used by different service institutions.

FIG. 20 shows a medical card where all the medical history is stored in electronic memories along with insurance information and photo identification, if desired. The photo can also be used on the UET card when it functions as an ID card, as shown in FIG. 21. Similarly, FIG. 22 shows a UET card functioning as a phone card. FIG. 23 shows a UET card functioning as a an airline travel card, and FIG. 24 shows a UET card functioning as a car rental card. For special cards, such as those shown in FIGS. 22, 23, and 24, special interfaces are required to handle protocols with pay phone, airline reservation systems, and car rental management systems. A diagram showing the relationships of those interfaces is shown in FIG. 25. These special interfaces are CIU with special software programs to interact with the existing systems, protocols and procedures.

As shown in FIG. 26, the UET card has ability to provide a complete alpha numeric keyboard on the touch screen, which is similar to the keyboard of a personal computer, and which can be used for utilities which require typing for special notes, such as those features provided in present day electronic diaries.

FIG. 27 shows an example of some miscellaneous features which may be included in the UET card. FIG. 28 outlines a "to do" feature, as it might appear on the display of the UET card, and which may be written through the keyboard described in relation to FIG. 26. An audible alarm/buzzer may be used in these applications as a reminder.

Figure 29:
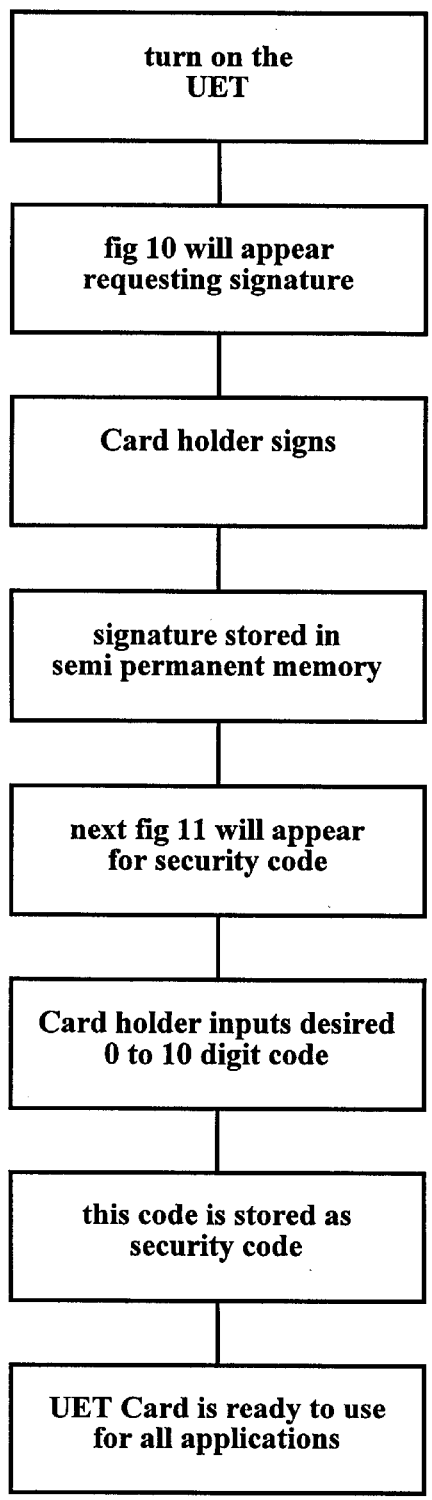
FIG. 29 outlines the initialization process for a UET card of the present invention.

FIG. 29 outlines an initialization process for a UET card. When the card is first purchased by a user, it will either have a default security code or no security codes, and it may be set by any user. To initialize the UET card, the user activates the power on/off switch 12, as shown in FIG. 1. The image shown in FIG. 10 will then appear on the display of the UET card. The user writes his or her signature on the display in the space indicated, and that signature is stored in semi-permanent memory. It is also possible to a provide special personal identification number instead of a signature to identify a valid customer. Next, the image shown in FIG. 11 will appear, requesting the user to input a security code. The user inputs a security code of up to 10 digits, for example (although the number of digits in the security code may vary, and is not limited to 10 digits). To do so, the user touches the numbers on the bottom of the display in the desired sequence. The user may use the "clear" or "clear all" keys to erase numbers erroneously entered. When the user is satisfied with the security code, the user uses the "enter" key to input the security code into semi-permanent memory. Thereafter, the UET card, or protected accounts and/or information in the card, cannot be used until the security code is entered. As an additional means of security, the UET card issuer may require that each user who purchases or receives a UET card register with a central security agency (which may be the UET card provider) to receive a personal identification number, which is different from the security code entered by the user in the UET card during initialization.

In order to activate the UET card for a particular credit card service or other service institution, the UET card user must complete the normal qualification steps required by the service institution. After the service institution approves the user, it notifies the user, and the user then connects the UET card to a CIU, which dials the number of a central computer which is enabled by the service institution to transmit the authorization data enabling the UET card to function as a "credit card" or other type of "card" for that institution. The service institution may then identify the user, either through a PIN code given to the user by the service institution (such as through the mail), or by other suitable means, such as caller identification of the user's phone number. Once the service institution has identified the user, it transmits to the UET card through the CIU the required information, such as the category of service institution, the date of issuance, the date of expiration, the credit limit, the card number, the name of the institution and/or an image of the institution, which may either be a name or, optionally, a graphic image of the service institution's logo. The service institution receives from the UET card, through the CIU, information concerning the user and the user's UET card, such as the unique serial number of the UET card, the UET user's electronic signature (stored in the UET card), and other relevant personal information of the user.

When a user desires to use a UET card for a transaction, the following sequence takes place. First, the user turns on the power for the UET card. Optionally, a security sequence may then take place. In that event, the user must then enter a security code within a predetermined amount of time, such as 10 seconds. If the user does not enter the correct security code within the predetermined amount of time, the card may prompt him or her to try again. The UET card may be programmed to permit the user a predetermined number of attempts, such as three attempts. If the user cannot enter the correct security code within the predetermined amount of time and within the predetermined number of attempts, the card may deactivate itself, so that it can no longer be used without re-authorization from the company which issued the UET card.

When the user enters the proper security code within the predetermined amount of time, the display shown in FIG. 12 will appear. The user may then select the type of transaction from a menu which includes choices such as credit card transactions, bank card transactions, retail credit transactions, medical or insurance transactions, personal identification, travel or telephone, or other miscellaneous transactions.

If the user selects a credit transaction, then an image such as that shown in FIG. 13 will appear. The user can then select one of a number of credit cards, such as the American Express card, and an image such as that shown on FIG. 14 will appear. Optionally, a security procedure may take place for the American Express card, which the user can activate by touching the SEC icon on the touch screen. If the security option has been preselected for the American Express card, then the American Express card may be used only if the proper security code is entered. Once the user has activated the American Express service on the UET card, the user then provides the UET card displaying the American Express image to a sales person. The sales person connects the UET card to the CIU, such as the CIU shown in FIG. 5, which is connected to a point of sales terminal. To initiate that transaction, the sales person enters the appropriate command on the keyboard or keypad on the CIU. The CIU receives the appropriate information from the UET card regarding the user's American Express account, such as the user's name, address, the UET serial number, the American Express account number, account expiration date, and PIN number. The CIU dials the telephone number of the American Express credit service, and when the telephone call is connected, it sends the information received from the UET card to the American Express credit service, plus information from the point of sales store, such as the retailer identification number, the amount of the transaction, etc. During the transaction, the display on the UET card may display the images shown in FIG. 15.

The American Express service then provides a credit check and, if appropriate, sends an authorization number to the CIU. At this juncture, the American Express service could, optionally, update the credit card information in the UET card for additional, dynamic, security. Security could be further improved by allowing the American Express service to modify or delete personal information, such as the user's signature, if the UET card were to be reported stolen or otherwise misused. After the CIU receives the authorization number, the user is then required to authorize the transaction, which is displayed on the UET card, by either signing the UET card, or on paper, or on some other device, and the user has the option of entering an amount for a tip or gratuity, as shown in FIG. 16. After the user signs for the transaction, the signature that the user entered upon initialization of the card appears, so that the user's signature may be checked. The user's signature may appear on the display of the UET card, or on the CIU, or on the display of the point of sales computer, or on any combination thereof. If the sales person is satisfied with the signature comparison, the sales person completes the transaction, and the CIU transmits completed details of the sales transaction to the point of sales computer, the UET card, and the American Express service. Those details include the date of the transaction, the amount, the name of the retail store or service (for the UET card and the American Express service records), the name of the customer (for the American Express and point of sales computers), etc.

Figure 30:
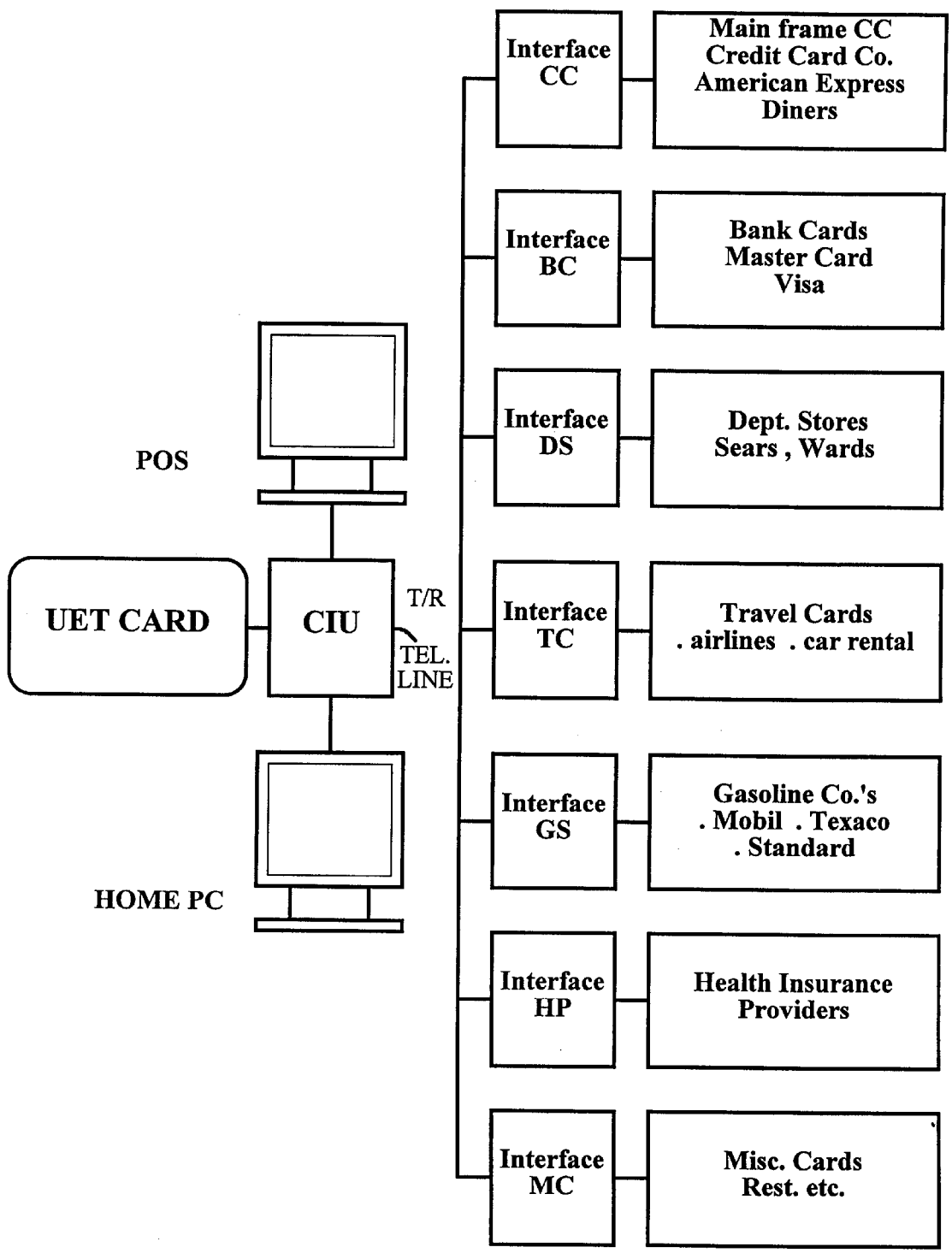
FIG. 30 illustrates a variety of interfaces for the UET card of the present invention.

FIG. 30 outlines a variety of interfaces which may be used in connection with the UET card. This includes interfaces for credit card companies, banks, department stores, travel service companies, gasoline companies, health service providers, and miscellaneous service providers, such as restaurants, etc.

Figure 31:
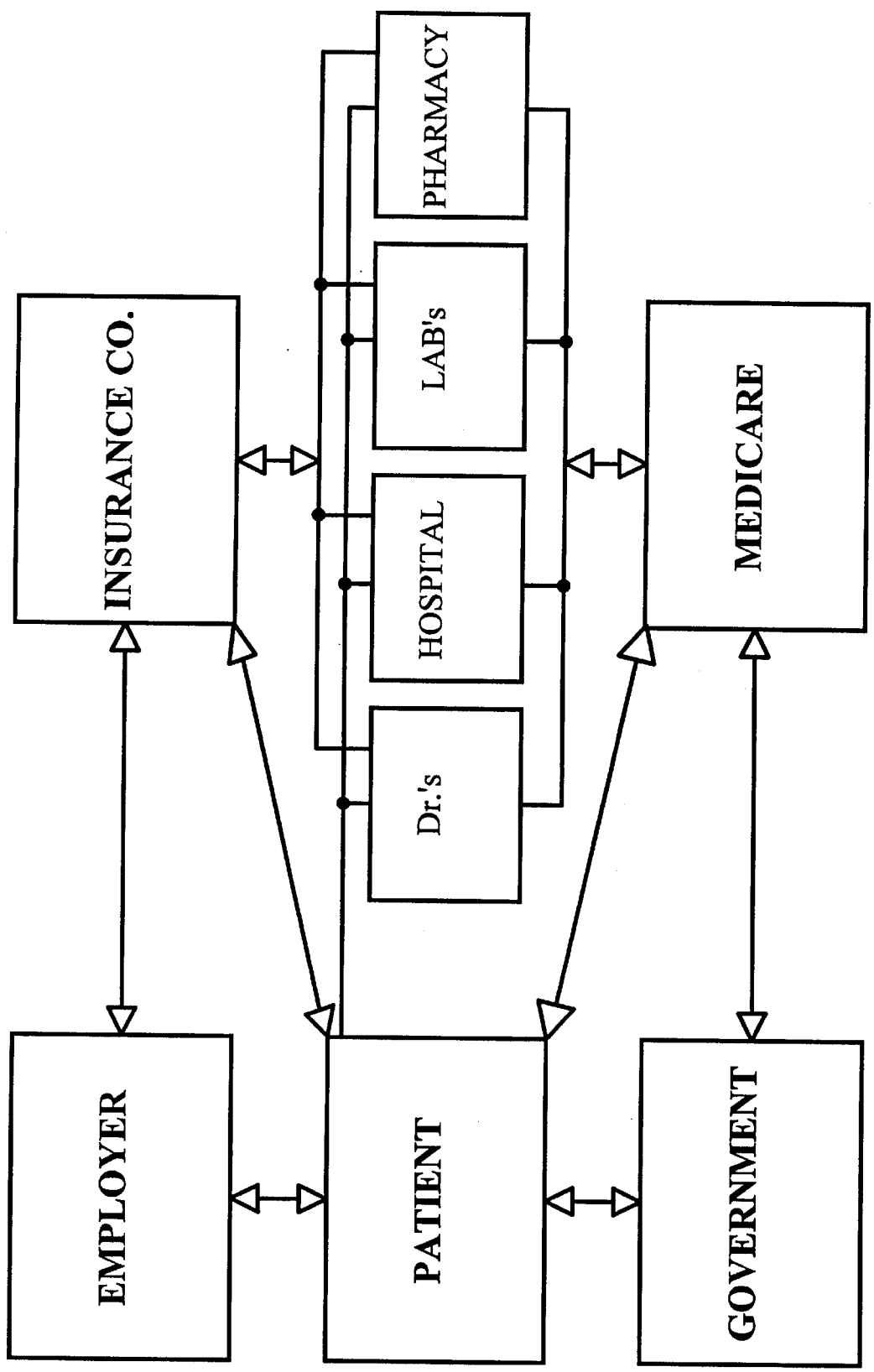
FIG. 31 illustrates a block diagram of a health care service provider system using the UET card of the present invention.

FIG. 31 is a diagram of a health service provider system which uses the UET card of the present invention, which includes patients who have UET cards. The patient's UET card includes, in memory, all or some of the patient's medical history, including allergies, potentially critical conditions, drug allergies, and the like. It also includes information concerning the patient's employer and health care insurer or insurers, which may include insurance companies or Medicare or Medicaid or other insurance organizations. The medical information also may include identifying information of the physicians, hospitals, laboratories, and pharmacies which have provided health care services for the patient.

When a patient visits a health care provider for treatment, laboratory work, or to purchase drugs, the UET card may be used in a manner similar to that of a credit card transaction. The UET card is connected to a CIU, which is connected to a personal computer (or other type of computer) used by the health care provider. In an emergency room setting, for example, the UET card may be used to instantly provide all of the information that is usually obtained through interviewing a patient or those who have brought the patient to the emergency room, thus providing instantaneous and accurate information in order to expedite the admittance and treatment of the patient.

At present significant health cost is attributed to paperwork. Through the use of the UET card as a health card, a substantial amount of such paperwork can be eliminated and transactions with doctors, hospitals and insurance companies can be conducted simultaneously in real time to resolve disputes and can be recorded electronically. It is this type of application of the UET card which makes the concept of super information highways practical and profitable. Unless these expensive paper transactions are eliminated, it will be difficult to improve productivity and efficiency and reduce management costs in all transactions, be it with banks, hospitals or shops.

I claim:

1. A universal electronic transaction card for storing, transmitting, and receiving information, including personal information for a user of the universal electronic transaction card, account information for accounts with service institutions in which the user has an account, and transactional information for accounts with service institutions in which the user has an account, for a plurality of service institutions, comprising:

a. housing means for housing inputting means, memory means, communications means, display means, and processing means, the housing means adapted to fit in a pocket or purse;

b. inputting means for inputting information, including personal information for the user, account information for a plurality of service institutions in which the user has an account, and transactional information for each service institution for which account information exists, into the memory means;

c. memory means for storing information, including personal information for the user, account information for a plurality of service institutions in which the user has an account, and transactional information for each service institution for which account information exists;

d. communications means for electronically communicating information, including personal information, account information, and transactional information, with service institutions;

e. display means for displaying information for a plurality of service institution accounts, including personal information, account information, and transactional information;

f. processing means for processing information, including personal information, account information, and transactional information;

g. means for providing and storing electric power, and, h. security means for preventing unauthorized use of the universal electronic transaction card and for preventing unauthorized access to the information stored in the memory means of the universal electronic transaction card.

2. The universal electronic transaction card of claim 1 further comprising a pointing device for inputting information.

3. The universal electronic transaction card of claim 2 in which the pointing device is selected from a group consisting of: a computer mouse pointing device and a computer trackball pointing device.

4. The universal electronic transaction card of claim 1 in which the inputting means includes means for inputting stored cash value information, the memory means includes means for storing stored cash value information, the communication means includes means for electronically communicating stored cash value information, the display means includes means for displaying stored cash value information, and the processing means includes means for processing stored cash value information.

5. The universal electronic transaction card of claim 1 in which the inputting means includes means for storing promotional information, the communications means includes means for electronically communicating promotional information, the display means includes means for displaying promotional information, and the processing means includes means for processing promotional information.

6. The universal electronic transaction card of claim 1 in which the security means includes means for displaying a photograph of the user.

7. The universal electronic transaction card of claim 1 in which the security means includes means for deactivating the universal electronic transaction card after an incorrect security code has been entered.

8. The universal electronic transaction card of claim 7 in which the means for deactivating the universal electronic transaction card is invoked after a predetermined number of unsuccessful attempts to enter a security code.

9. The universal electronic transaction card of claim 1 in which the security means includes means for identifying a user by finger print.

10. The universal electronic transaction card of claim 1 in which the security means includes means for identifying a user by voice print.

11. The universal electronic transaction card of claim 1 in which the security means includes means for deleting account information.

12. The universal electronic transaction card of claim 1 in which the security means includes means for deleting personal information.

13. The universal electronic transaction card of claim 1 further including a unique universal electronic transaction card identification number.

14. The universal electronic transaction card of claim 1 in which the display means concurrently displays a plurality of categories of information.

15. The UET card of claim 1 in which caller identification data is stored in the UET card along with each transaction.

16. A universal electronic transactions card and communications system for storing, transmitting, and receiving information, including personal information for a user of the universal electronic transaction card, account information for accounts with service institutions in which the user has an account, and transactional information for accounts with service institutions in which the user has an account, for a plurality of service institutions, including at least one universal electronic transactions card adapted to fit in a pocket or a purse and at least one communications interface unit, comprising:

a. inputting means for inputting information, including personal information for the user, account information for a plurality of service institutions in which the user has an account, and transactional information for each service institution for which account information exists, into memory means in the universal electronic transactions card;

b. memory means in the universal transactions card for storing information, including personal information for the user, account information for a plurality of service institutions in which the user has an account, and transactional information for each service institution for which account information exists;

c. communications means for electronically communicating information to and from the memory means, including personal information, account information, and transactional information, with service institutions;

d. display means for displaying information for a plurality of service institution accounts, including personal information, account information, and transactional information; and e. processing means for processing information, including personal information, account information, and transactional information;

f. means for providing and storing electric power; and, g. security means for preventing unauthorized use of the universal electronic transaction card and for preventing unauthorized access to the information stored in the memory means of the universal electronic transaction card.

17. The universal electronic transaction card and communications system of claim 16 in which the means for providing and storing electric power includes a rechargeable battery.

18. The universal electronic transactions card and communications system of claim 16 in which the means for providing and storing electric power includes a conductive path which is established where the universal electronic transaction card is connected to a communications interface unit.

19. The universal electronic transactions card and communications system of claim 16 in which the inputting means comprises an interface for receiving electronic information comprising at least one electrically conductive connector for directly electrically connecting to a transactional communications system to electronically receive transactional information therefrom.

20. The universal electronic transaction card and communications system of claim 16 in which the communications interface unit comprises a passive interface between the universal electronics transaction card and a personal computer.

21. The universal transaction card and communications system of claim 20 in which the communications interface unit further comprises means for recharging the means for providing and storing electric power in the universal electronic transactions card.

22. The universal electronic transaction card and communications system of claim 16 in which the communications interface unit comprises a passive interface with the universal electronics transactions card and a modem.

23. The universal transaction card and communications system of claim 22 in which the communications interface unit further comprises means for recharging the means for providing and storing electric power in the universal electronic transactions card.

24. The universal electronic transaction card and communications system of claim 16 in which the communications interface unit comprises a passive interface with the universal electronics transactions card, a modem, means for processing information, means for storing information, input means for entering information, and display means for displaying information.

25. The universal transaction card and communications system of claim 24 in which the communications interface unit further comprises means for recharging the means for providing and storing electric power in the universal electronic transactions card.

26. A health care management system comprising a. at least one universal electronic transaction card for inputting, storing, processing, and transmitting personal information, including personal medical history, account information, and transactional information, including substantially all information normally recorded on a paper receipt;

b. at least one central health care information processing system, including means for creating, assigning and storing patient and health care provider accounts; means for electronically communicating account information to a universal electronic transaction card; means for receiving and storing personal information for each authorized account number; means for communicating with a universal electronic transaction card to authorize account transactions, means for receiving and storing information relating to account transactions; and means for storing and communicating medical histories;

c. at least one health care provider processing system, including means for electronically communicating with the central health care information processing system; means for electronically communicating with the universal electronic transaction card; and memory means for storing patient information; and, d. at least one communications system for providing communications between the universal electronic transaction card, the central health care information processing system, and the health care provider processing system.

27. The health care management system of claim 26, further including card interfacing means for interfacing between the health care provider processing system and the central health care information processing system.

28. A method of issuing an account by a service institution to a user of a universal electronic transaction card to authorize the user to use the universal electronic transaction card for the account comprising:

a. obtaining predetermined information from the user as required by the service institution;

b. issuing account information for the user, including an account number;

c. establishing an electronic communication between the user's universal electronic transaction card and the service institution;

d. monitoring security information to identify the universal electronic transaction card and the user of the universal electronic transaction card; and e. electronically transmitting to the user's universal electronic transaction card predetermined account information for the service institution account and predetermined information about the service institution and the account to be displayed by the universal electronic transaction card when the universal electronic transaction card is used to conduct a credit transaction for such account.

29. The method of claim 28 in which predetermined information includes the name of the service institution account service and a graphic image of the service institution's account service logo.

30. The method of claim 28 in which the security information includes a universal electronic transactions card identification number.

31. The method of claim 28 in which the security information includes caller identification data.

32. The method of claim 28 in which the security information includes a personal identification number entered by the user.

* * * * *